United States Patent [19]
Wallace et al.

[11] Patent Number: 5,836,871
[45] Date of Patent: Nov. 17, 1998

[54] METHOD FOR LIFTING A BODY WALL USING AN INFLATABLE LIFTING APPARATUS

[75] Inventors: Daniel T. Wallace, Mountain View; Jeffery A. Smith, Sunnyvale; Richard Mueller, Byron; Joseph Mandato, Atherton; Frederic H. Moll, San Francisco, all of Calif.

[73] Assignee: Origin Medsystems, Inc., Menlo Park, Calif.

[21] Appl. No.: 660,728

[22] Filed: Jun. 10, 1996

Related U.S. Application Data

[63] Continuation of Ser. No. 239,348, May 6, 1994, abandoned, which is a continuation-in-part of Ser. No. 794,590, Nov. 19, 1991, Pat. No. 5,309,896, which is a continuation-in-part of Ser. No. 706,781, May 29, 1991, abandoned, said Ser. No. 239,348, is a continuation-in-part of Ser. No. 62,707, May 18, 1993, Pat. No. 5,520,609, which is a continuation of Ser. No. 706,781, said Ser. No. 239,348, is a continuation-in-part of Ser. No. 134,573, Oct. 8, 1993, Pat. No. 5,425,357, which is a continuation-in-part of Ser. No. 794,590.

[51] Int. Cl.$^6$ .................................................. A61M 29/02
[52] U.S. Cl. ............................................ 600/204; 600/207
[58] Field of Search ........................... 606/192; 600/204, 600/207; 604/101

[56] References Cited

U.S. PATENT DOCUMENTS

| | | |
|---|---|---|
| 1,735,519 | 11/1929 | Vance . |
| 2,663,020 | 12/1953 | Cushman . |
| 3,039,468 | 1/1959 | Price . |

(List continued on next page.)

FOREIGN PATENT DOCUMENTS

| | | | |
|---|---|---|---|
| 0 499 663 A3 | 10/1990 | European Pat. Off. | ........ A61B 17/02 |
| 0 411 767 A1 | 2/1991 | European Pat. Off. | ........ A61B 19/00 |
| WO 91/01687 | 2/1991 | European Pat. Off. | .......... A16B 8/12 |

(List continued on next page.)

OTHER PUBLICATIONS

R. Wittmoser, "Retroperitoneoscopy: A Preliminary Report", *Endoscopy*, 1976, pp. 760–761.

Charles G. Neumann, M.D., "The Expansion of The Area of the Skin by Progressive Disention of a Subsutaneous Ballon", Plastic and Reconstructive Surgery, Feb. 1957, vol. 19,No. 2, pp. 124–130.

(List continued on next page.)

*Primary Examiner*—Michael H. Thaler
*Attorney, Agent, or Firm*—Limbach & Limbach L.L.P.

[57] ABSTRACT

An apparatus deployed through a laparoscopic incision in a body wall to apply an external lifting force over a large area of the body wall. The apparatus comprises a body wall engaging element and an elongate lifting member. The body wall engaging element is capable of passing in a packaged state through the laparoscopic incision, is inflatable to an inflated state, and includes, in the inflated state, a plane lifting surface. The elongate lifting member includes a distal portion connected to the plane lifting surface, and capable of passing through the laparoscopic incision. A proximal portion receives the external lifting force in a direction that moves the body wall engaging element into contact with the body wall. A method for lifting a body wall by applying an external lifting force to a large area of the body wall through a laparoscopic incision. The lifting device is provided that includes an body wall engaging element capable of passing through the laparoscopic incision in a packaged state. The lifting device also includes a lifting member including a distal portion to which the body wall engaging element is connected. The body wall engaging element and the distal portion of the lifting member are advanced through the laparoscopic incision. The body wall engaging element is inflated to an inflated state to provide a plane lifting surface. Finally, the external lifting force is applied to the proximal portion of the lifting member to move the lifting surface into contact with the body wall.

2 Claims, 17 Drawing Sheets

U.S. PATENT DOCUMENTS

| | | | |
|---|---|---|---|
| 3,774,596 | 11/1973 | Cook | 128/5 |
| 3,782,370 | 1/1974 | McDonald | 128/20 |
| 3,800,788 | 4/1974 | White | 128/83 |
| 3,817,251 | 6/1974 | Hasson | 128/348 |
| 3,831,587 | 8/1927 | Boyd | 128/6 |
| 3,863,639 | 2/1975 | Kleaveland | 128/303 |
| 3,882,852 | 5/1975 | Sinreich | 128/4 |
| 3,961,632 | 6/1976 | Mossun | 127/347 |
| 4,052,980 | 10/1977 | Grams et al. | 128/18 |
| 4,077,412 | 3/1978 | Moossun | 128/347 |
| 4,083,369 | 4/1978 | Sinnreich | 128/276 |
| 4,137,906 | 2/1979 | Akiyama et al. | 128/2 |
| 4,157,085 | 6/1979 | Austad | 128/1 |
| 4,165,746 | 8/1979 | Burgin | 128/321 |
| 4,198,981 | 4/1980 | Sinnreich | 128/344 |
| 4,217,889 | 8/1980 | Radovan et al. | 128/1 |
| 4,240,102 | 1/1980 | Guiset | 3/1.4 |
| 4,240,433 | 12/1980 | Bordow | 128/276 |
| 4,263,900 | 4/1981 | Nicholson | 128/20 |
| 4,271,839 | 6/1981 | Fogarty et al. | 128/344 |
| 4,291,687 | 9/1981 | Sinnreich | 128/129 |
| 4,318,410 | 3/1982 | Chin | 128/325 |
| 4,430,076 | 2/1984 | Harris | 604/94 |
| 4,447,227 | 5/1984 | Kotsanis | 604/101 |
| 4,459,978 | 7/1984 | Kotsanis | 128/20 |
| 4,493,711 | 1/1985 | Chin et al. | 604/271 |
| 4,574,780 | 3/1986 | Manders | 128/1 |
| 4,612,938 | 9/1986 | Dietrich et al. | 128/655 |
| 4,615,704 | 10/1986 | Frisch | 623/8 |
| 4,622,955 | 11/1986 | Fakhrai | 128/20 |
| 4,651,717 | 3/1987 | Jakubczak | 128/344 |
| 4,666,447 | 5/1987 | Smith et al. | 623/8 |
| 4,693,243 | 9/1987 | Buras | 128/207.15 |
| 4,710,181 | 12/1987 | Fuqua | 606/192 X |
| 4,719,918 | 1/1988 | Bonomo et al. | 128/344 |
| 4,763,653 | 8/1988 | Rockey | 128/344 |
| 4,779,611 | 10/1988 | Grooters et al. | 128/4 |
| 4,800,901 | 1/1989 | Rosenberg | 128/899 |
| 4,803,029 | 2/1989 | Iversen et al. | 264/264 |
| 4,863,440 | 9/1989 | Chin | 604/271 |
| 4,944,443 | 7/1990 | Oddsen et al. | 227/19 |
| 4,949,718 | 8/1990 | Neuwirth et al. | 128/401 |
| 4,966,583 | 10/1990 | Debbas | 604/98 |
| 4,976,710 | 12/1990 | Mackin | 606/15 |
| 4,984,564 | 1/1991 | Yuen | 128/20 |
| 5,002,557 | 3/1991 | Hasson | 606/191 |
| 5,082,005 | 1/1992 | Kaldany | 128/850 |
| 5,103,804 | 4/1992 | Abele et al. | 128/4 |
| 5,109,875 | 5/1992 | Gottlieb | 128/899 |
| 5,116,357 | 5/1992 | Eberbach | 606/213 |
| 5,122,122 | 6/1992 | Allgood | 604/174 |
| 5,122,155 | 6/1992 | Eberbach | 606/213 |
| 5,141,515 | 8/1992 | Eberbach | 606/151 |
| 5,152,279 | 10/1992 | Wilk | 128/17 |
| 5,158,548 | 10/1992 | Lau et al. | 604/96 |
| 5,159,925 | 11/1992 | Neuwirth et al. | 128/401 |
| 5,163,949 | 11/1992 | Bonutti | 606/192 |
| 5,176,128 | 1/1993 | Andrese | 128/20 |
| 5,176,692 | 1/1993 | Wilk et al. | 606/151 |
| 5,176,697 | 1/1993 | Hasson et al. | 606/191 |
| 5,178,133 | 1/1993 | Pena | 128/20 |
| 5,183,033 | 2/1993 | Wilk | 128/20 |
| 5,183,463 | 2/1993 | Debbas | 604/98 |
| 5,183,464 | 2/1993 | Dubrul et al. | 604/96 |
| 5,183,468 | 2/1993 | McLees | 604/164 |
| 5,185,596 | 2/1993 | Condon et al. | 604/101 |
| 5,188,602 | 2/1993 | Nichols | 604/113 |
| 5,188,630 | 2/1993 | Christoudias | 606/1 |
| 5,195,507 | 3/1993 | Bilweis | 128/20 |
| 5,197,948 | 3/1993 | Ghodsian | 604/30 |
| 5,197,971 | 3/1993 | Bonutti | 606/192 |
| 5,235,966 | 8/1993 | Jamner | 128/20 |
| 5,257,977 | 11/1993 | Eshel | 604/113 |
| 5,269,753 | 12/1993 | Wilk | 604/49 |
| 5,280,782 | 1/1994 | Wilk | 128/20 |
| 5,293,863 | 3/1994 | Zhu et al. | 128/20 |
| 5,308,327 | 3/1994 | Heaven et al. | 604/96 |
| 5,318,012 | 6/1994 | Wilk | 128/20 |
| 5,318,013 | 6/1994 | Wilk | 128/20 |
| 5,331,975 | 7/1994 | Bonutti | 128/898 |
| 5,339,801 | 8/1994 | Poloyko et al. | 128/20 |
| 5,351,679 | 10/1994 | Mayzels et al. | 128/20 |
| 5,359,995 | 11/1994 | Sewell, Jr. | 128/20 |
| 5,514,091 | 5/1996 | Yoon | 600/207 X |
| 5,520,609 | 5/1996 | Moll et al. | 600/207 X |
| 5,522,790 | 6/1996 | Moll et al. | 600/207 X |
| 5,527,264 | 6/1996 | Moll et al. | 600/207 X |

FOREIGN PATENT DOCUMENTS

| | | | |
|---|---|---|---|
| WO 91/14392 | 10/1991 | European Pat. Off. | A61B 1/00 |
| 464 463-A | 1/1992 | European Pat. Off. | A61B 17/28 |
| WO 92/18056 | 10/1992 | European Pat. Off. | A61B 17/02 |
| 9102759 U | 7/1991 | Germany | A61B 17/02 |
| 9104383 U | 7/1991 | Germany | A61B 17/02 |
| 9202305 U | 6/1992 | Germany | A61B 19/00 |
| 797668 | 6/1978 | Russian Federation | A16B 17/02 |
| 502331 | 9/1937 | United Kingdom . | |

OTHER PUBLICATIONS

M.M. Gazayerli, "The Gazayerli Endoscopic Retractor* Model 1, " Surgical Laparoscopy and Endoscopy, vol. 1, No. 2, 1991, pp. 98–100.

N. Kayakawa, et al., "Laparoscopic Cholecystectomy Using Retraction of the Falciform Ligament," Surgical Laparoscopy and Endoscopy, vol. 1, No. 2, 1991, p. 126.

Geza J. Jako & Stephen Rozsos, "Preliminary Report: Endoscopic Laser Microsurgical Removal of Human Gallbladder," J. Laparoendoscopic Surgery, vol. 1, No. 4, 1991.

A.G. Gordon, et al., "The Develoopment of Laparoscopy Surger," Bailliére's Clinical Obstetrics and Gynaecology, vol. 3, No. 3, Sep. 1989, pp. 429–449.

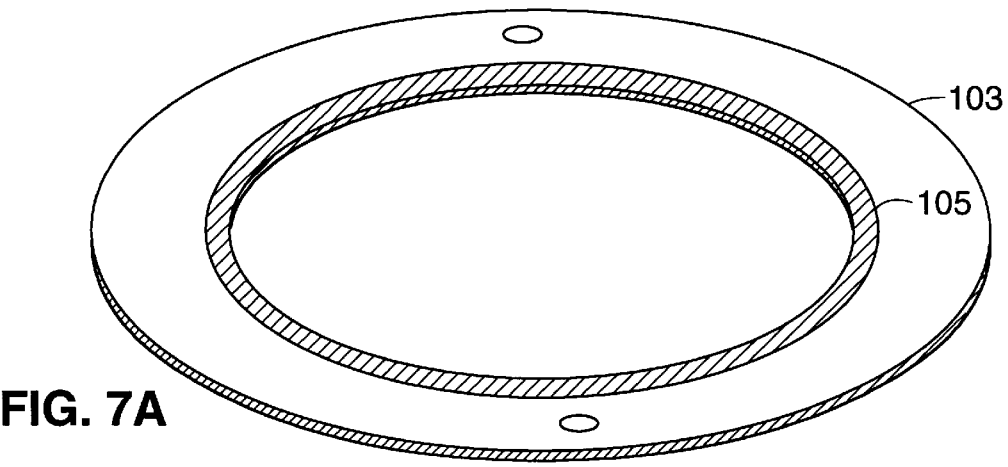
FIG. 7A
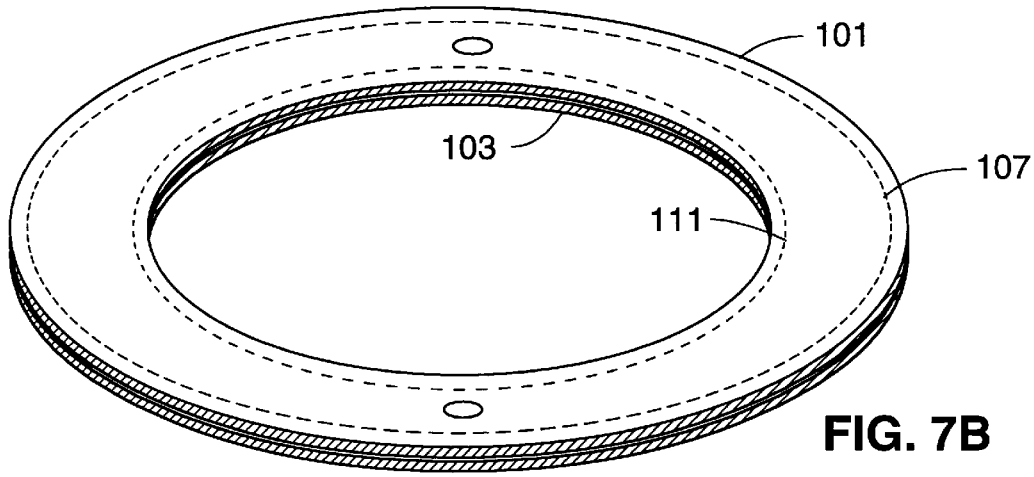
FIG. 7B
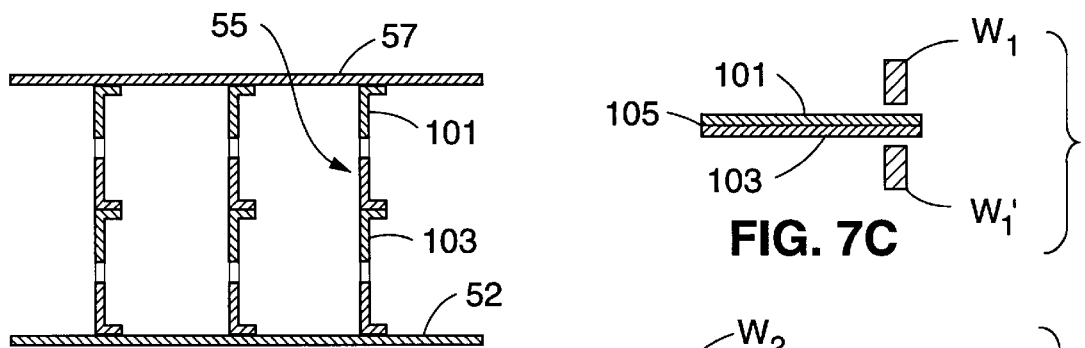
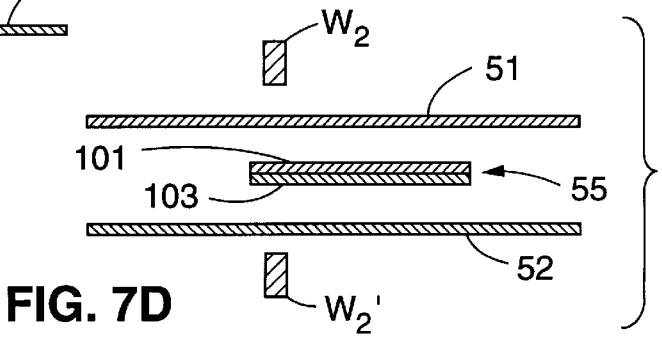
FIG. 7C
FIG. 7E
FIG. 7D

METHOD FOR LIFTING A BODY WALL USING AN INFLATABLE LIFTING APPARATUS

PRIOR APPLICATIONS

This application is a continuation of application Ser. No. 08/239,348 filed May 6, 1994, now abandoned, which is a Continuation-in-Part of prior application Ser. No. 07/794,590, filed 19 Nov. 1991, now U.S. Pat. No. 5,309,896 of inventors Frederic H. Moll, Charles Gresl, Jr., Albert K. Chin, and Philip K. Hopper, which is a Continuation-in-Part of prior application Ser. No. 07/706,781, filed 29 May 1991 and now abandoned, of Frederic H. Moll, Albert K. Chin, Diane E. Caramore, and Frank T. Watkins III. Application Ser. No. 08/239,348 is also a Continuation-in-Part of pending prior application Ser. No. 08/062,707, filed 18 May 1993, now U.S. Pat. No. 5,520,609 of Frederic H. Moll, Albert K. Chin, Diane E. Caramore, and Frank T. Watkins III, which is a Continuation the above-mentioned prior application Ser. No. 07/706,781. Application Ser. No. 08/239,348 is also a Continuation-in-Part of prior application Ser. No. 08/134,573 of Frederic H. Moll, Daniel T. Wallace, Jeffrey, A. Smith, David C. Forster, and Albert K. Chin, filed 8 Oct. 1993, now U.S. Pat. No. 5,425,357 which is a Continuation-in-Part of the above-mentioned prior application Ser. No. 07/794,590.

FIELD OF THE INVENTION

The invention generally relates to an apparatus for lifting or retracting tissue during surgery, especially during laparoscopic surgery.

BACKGROUND OF THE INVENTION

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for various procedures including suturing hernias. U.S. Pat. Nos. 4,919,152 and 4,944,443 are concerned with techniques for suturing hernias. Another recent innovation is the use of laparoscopic surgery for removing the gallbladder.

In the course of performing laparoscopic procedures in the abdomen, it is necessary to raise the abdominal wall to create space in which to work. A well-known method of raising the abdominal wall is to insufflate the abdominal cavity with a suitable insufflation gas, such as air, or carbon dioxide. A significant disadvantage of gas insufflation is that elongated instruments must be passed into the abdominal cavity through gas-tight seals, which significantly reduce the surgeon's feel of the instruments.

Several mechanical alternatives to gas insufflation have been proposed. The Gazayerli Endoscopic Retractor Model 1, described in SURGICAL LAPAROSCOPY AND ENDOSCOPY, Vol. 1, No. 2, 1991, pages 98–100, has a rigid rod with a hinged blade at the distal end. The blade can rotate through 360 degrees about an axis perpendicular to the long axis of the rod. The blade is aligned with the long axis of the rod for insertion into the abdomen through a small puncture. Once inside the abdomen, the blade is swivelled through about 90 degrees to form a T-shaped structure. The proximal end of the rod can be raised by hand or by a rope, pulley and weight arrangement. Raising the rod causes the blade to engage the abdominal wall and to lift it.

French patent application no. 90-03980 shows a wire structure that is threaded into the abdomen through a small puncture to engage and to lift the abdominal wall. The application also shows a fan retractor that has a first angle-shaped member having a first leg that engages with the abdominal wall, a tubular second leg having a bore, and a third leg, remote from the first leg, that has a hook-shaped member on its end distal from the second leg. A second angle-shaped member has a first leg that engages with the abdominal wall, a second leg that pivots within the bore of the second leg of the first angle-shaped member, and a third leg, remote from the first leg, that serves as an operating lever for the second angle-shaped member. The first legs of the angle-shaped members are closed together to insert them into the abdominal cavity through an incision. The third leg of the second angle-shaped member is then operated to spread the first leg of the second angle-shaped member apart from the first leg of the first angle-shaped member. The first legs are engaged with the peritoneum inside the abdominal cavity. A lifting force is then applied to the hook-shaped member to lift the retractor and hence to lift the abdominal wall.

U.S. patent application Ser. No. 08/062,707, the application of which this application is a Continuation-in-Part, describes a number of different mechanical devices that are inserted through one or more punctures into the abdomen. All or part of the device is then lifted to lift the abdominal wall away from the underlying abdominal organs. One of the devices described in this prior application is a fan retractor that is inserted in a closed condition into the abdominal cavity, spread apart once inside the abdominal cavity, and brought into contact with the peritoneum inside the abdominal cavity. The apparatus is then lifted to lift the abdominal wall.

The above-mentioned fan retractors are all intended for intra-abdominal placement. It is difficult to place the peritoneum-engaging elements of such devices inside the abdominal cavity adjacent to the peritoneum without snagging the bowel or omentum. It is often necessary to make multiple attempts at inserting the retractor before the fan retractor can be correctly positioned with its peritoneum-engaging elements adjacent to the peritoneum with no bowel or omentum caught between the peritoneum-engaging elements and the peritoneum. Insufflating the abdomen before inserting the fan retractor does not eliminate the risk of snagging.

U.S. patent application Ser. No. 07/890,033 describes a fan retractor that is intended for insertion into the abdomen properitoneally to prevent snagging. The abdominal wall contacting legs of the fan retractor are shaped to enable them to dissect the peritoneum away from the abdominal wall so that the peritoneum can act as a drape over the underlying organs. In addition, the legs are shaped to provide a stiffness that decreases away from the pivot to enable the legs to conform to the internal shape of the abdominal wall. This reduces the risk of the ends of the legs piercing or otherwise causing trauma to the abdominal wall.

The known mechanical lifting devices described above expose a smaller area of the underlying organs than conventional gas insufflation. Moreover, the known mechanical lifting devices are inserted into the abdomen through a laparoscopic incision. Consequently, due to the dimensional constraints imposed by the need to pass though such an incision, these devices apply the lifting force to a relatively small area of the abdominal wall, and, consequently, expose the small area of the abdominal wall to a relatively high lifting pressure. Care must be exercised to prevent the lifting pressure from causing trauma to the area of the abdominal wall contacted by the mechanical lifting device.

OBJECTS AND SUMMARY OF THE INVENTION

It is an object of the invention to provide a body wall lifting device that is capable of lifting a body wall to expose an area of the underlying organs comparable with the exposure provided by conventional gas insufflation.

It is a further object of the invention to provide a body wall lifting device that is capable of lifting a body wall without subjecting the body wall to a lifting pressure significantly greater than that imposed by conventional gas insufflation.

It is a further object of the invention to provide a body wall lifting device that is capable of being passed through a laparoscopic incision in the body wall.

It is a further object of the invention to provide a body wall lifting device that is capable of lifting a selected portion of a body wall determined by the one or ones of the underlying organs to be treated.

It is a further object of the invention to provide a body wall lifting device that is capable of attaining the above objects without the known disadvantages of conventional gas insufflation.

It is a further object of the invention to provide a body wall lifting device that is capable of attaining the above objects without obstructing access for treating the exposed underlying organs.

It is a further object of the invention to provide a body wall lifting device that is capable of being used together with an auxiliary retractor that retracts organs underlying the lifted portion of the body wall.

Accordingly, the invention provides an apparatus for deployment through a laparoscopic incision in a body wall to apply an external lifting force over a large area of the body wall. The apparatus comprises a body wall engaging element and an elongate lifting member. The body wall engaging element is capable of passing in a packaged state through the laparoscopic incision. The body wall engaging element is inflatable to an inflated state, and includes, in the inflated state, a plane lifting surface. The elongate lifting member includes a distal portion that is connected to the lifting surface of the body wall engaging element, and is capable of passing through the laparoscopic incision. The elongate lifting member also includes a proximal portion that receives the external lifting force in a direction that moves the body wall engaging element into contact with the body wall.

The invention also provides a method for lifting a body wall by applying an external lifting force to a large area of the body wall through a laparoscopic incision. In the method, a lifting device is provided. The lifting device includes an body wall engaging element in a packaged state that is capable of passing through the laparoscopic incision. The lifting device also includes a lifting member that includes a distal portion to which the body wall engaging element is connected. The body wall engaging element and the distal portion of the lifting member are advanced through the laparoscopic incision. The body wall engaging element is inflated to an inflated state to provide a plane lifting surface. Finally, the external lifting force is applied to the proximal portion of the lifting member to move the lifting surface into contact with the body wall.

The invention finally provides an apparatus for deployment through a laparoscopic incision in a body wall to apply an external retraction force over a large area of an organ underlying the body wall. The apparatus comprises a retraction element and an operating member. The retraction element is capable of passing in a packaged state through the laparoscopic incision, and is inflatable to an inflated state. In the inflated state, the retraction element includes a plane retraction surface. The elongate operating member includes a distal portion that is connected to the retraction element and is capable of passing through the laparoscopic incision. The elongate operating member also includes a proximal portion that receives the external retraction force in a direction that moves the retraction surface into contact with the organ.

BRIEF DESCRIPTION OF THE DRAWINGS

FIGS. 7A–7E illustrate the process by which the baffles are formed and attached to the upper and lower envelope halves:

FIG. 7A is a perspective view showing the area in which a welding release agent is applied to the lower baffle half.

FIG. 7B is a perspective view showing the line along which the upper and lower baffle halves are welded together, and the line on which the upper and lower baffle halves are respectively welded to the upper and lower envelope halves.

FIG. 7C is a cross-sectional view showing how the baffle halves are welded together.

FIG. 7D is a cross-sectional view showing how the assembled baffle is welded to the envelope halves.

FIG. 7E is a cross-sectional view showing the completed envelope half and baffle assembly in its inflated state.

FIG. 10A shows the location of the laparoscopic incision.

FIG. 10B shows the inflating lifting device in its packaged state with its distal end inserted into the laparoscopic incision.

FIG. 10C shows the inflating lifting device in its packaged state inserted into the abdominal cavity, prior to releasing the envelope of the body wall engaging element from the sleeve.

FIG. 10D shows the inflating lifting device after the body wall engaging element has been partially inflated to rupture the sleeve. Arrows indicate how the body wall engaging element expands laterally and contracts axially when inflated.

FIG. 10E shows the inflating lifting device attached to the lifting arm with the body wall engaging element in its fully-inflated state, prior to raising the abdominal wall.

FIG. 10F shows the inflating lifting device attached to the lifting arm after the lifting arm has applied the lifting force to raise the abdominal wall.

FIG. 10G shows the inflating lifting device gripped by the surgeon's hand with the body wall engaging element in its fully inflated state, prior to raising the abdominal wall.

FIG. 10H shows the inflating lifting device gripped by the surgeon's hand after the surgeon has applied the lifting force to raise the abdominal wall.

FIG. 12A shows the abdominal wall after it has been lifted by the inflating lifting device.

FIG. 12B shows the auxiliary retractor inserted in its packaged state through the bore of the lifting tube of the lifting device.

FIG. 12C shows the auxiliary retractor after it has been inflated to its inflated state, prior to retracting the organ.

FIG. 12D shows the auxiliary retractor after it has been slid distally relative to the inflating lifting device to retract the organ.

DETAILED DESCRIPTION OF THE INVENTION

Figure 1A:
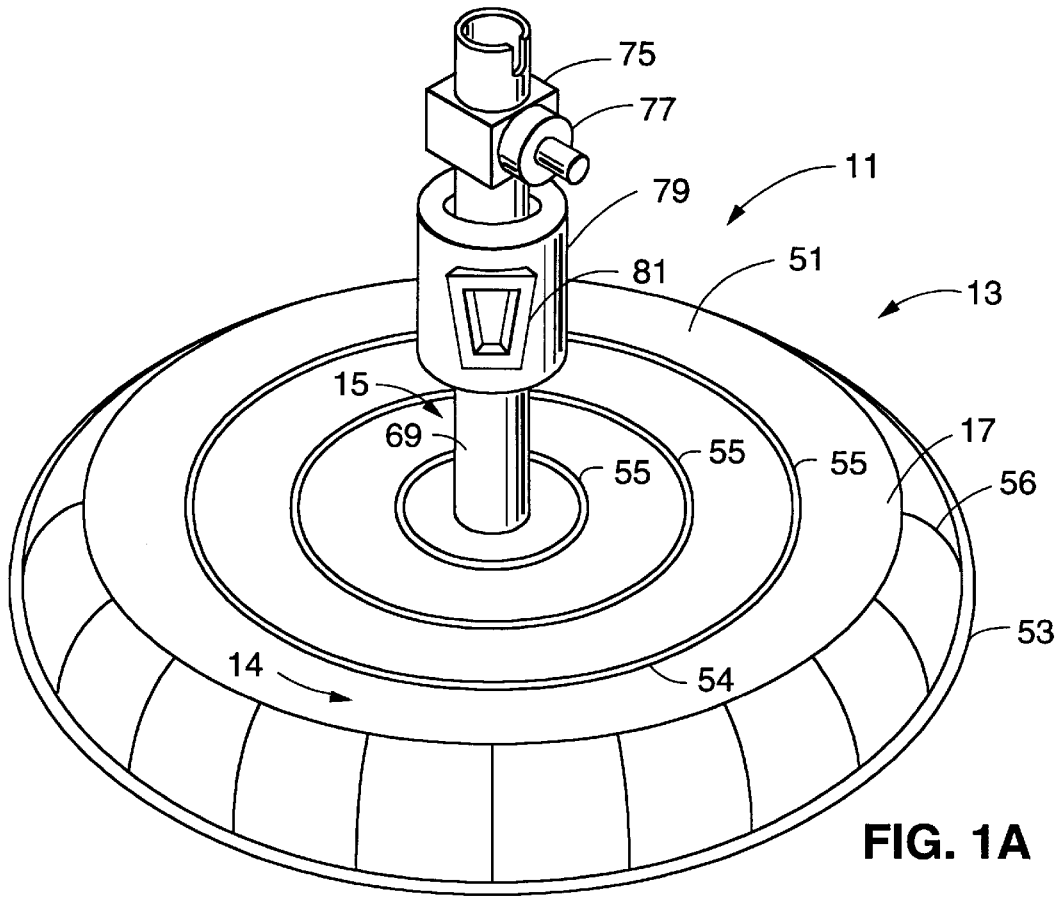
FIG. 1A is a perspective view of a first embodiment of the inflating lifting device according to the invention in its inflated state.
Figure 1B:
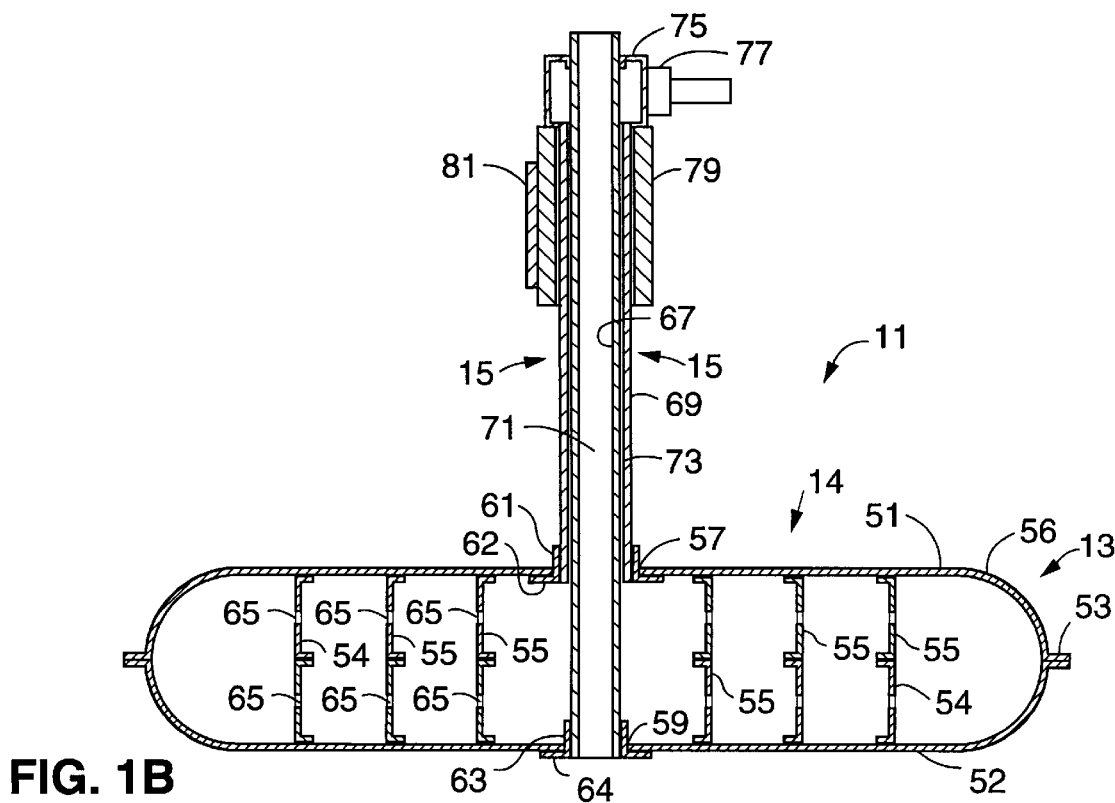
FIG. 1B is a cross-sectional view of the first embodiment of the inflating lifting device according to the invention in its inflated state.
Figure 1C:
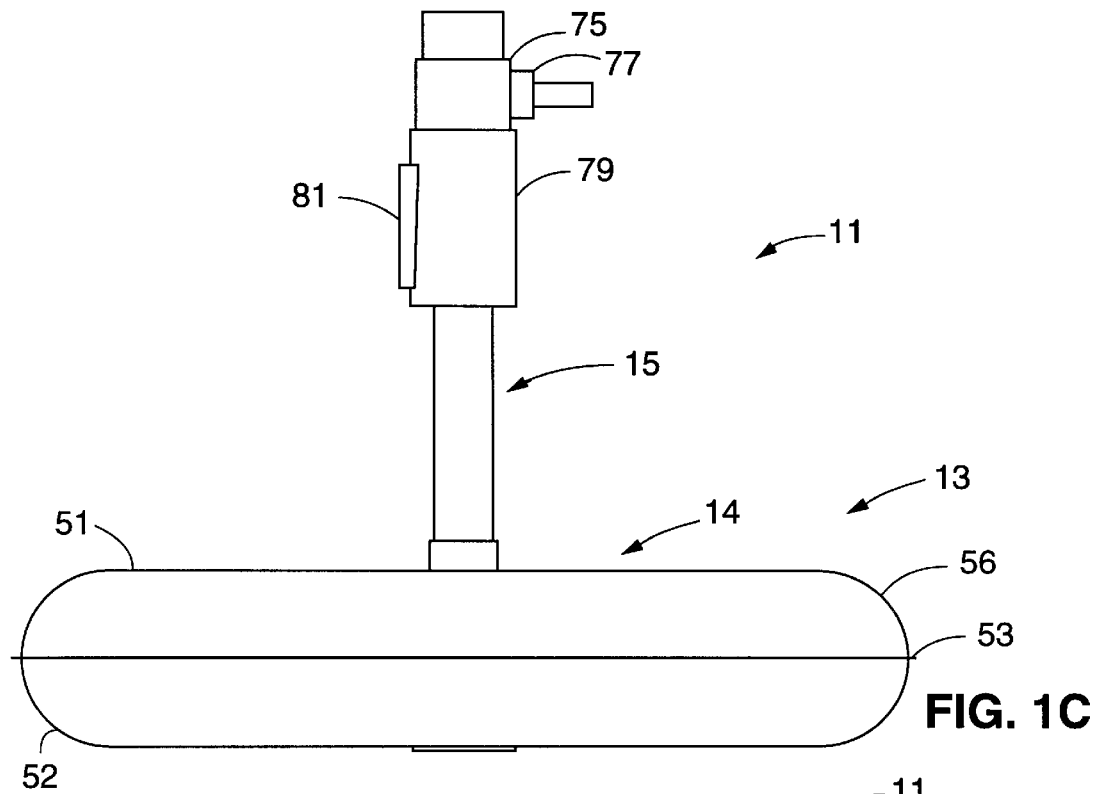
FIG. 1C is a side view of the first embodiment of the inflating lifting device according to the invention in its inflated state.
Figure 2A:
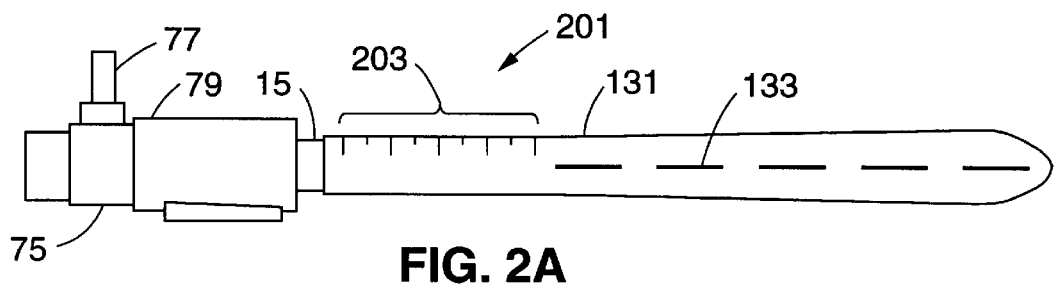
FIG. 2A is a side view of the first embodiment of the inflating lifting device according to the invention in its packaged state.
Figure 2B:
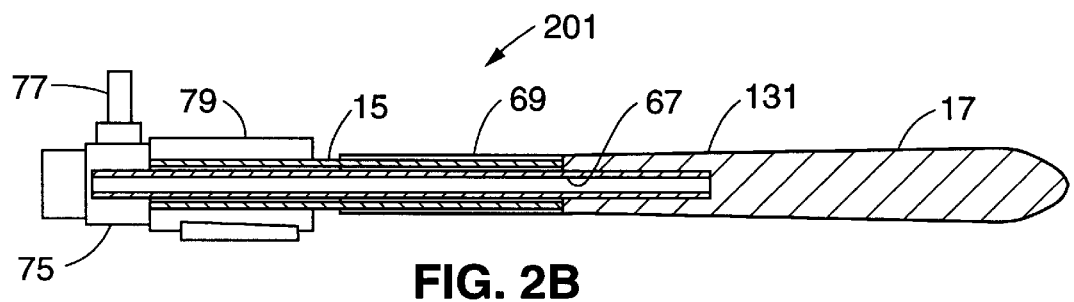
FIG. 2B is a cross-sectional view of the first embodiment of the inflating lifting device according to the invention in its packaged state.
Figure 2C:
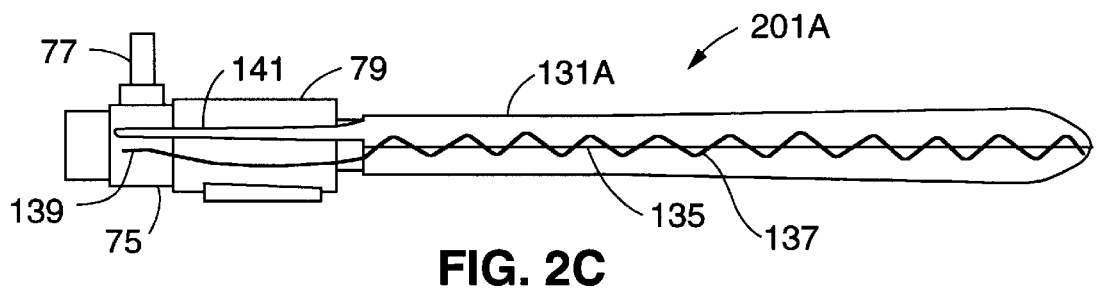
FIG. 2C is a side view of the first embodiment of the inflating lifting device according to the invention in its packaged state showing an alternative embodiment of the sleeve.

The inflating lifting device 11 according to the invention is shown with the body wall engaging element 13 in its inflated state in FIGS. 1A–1C, and is shown in its packaged state, prior to insertion into a body cavity, FIGS. 2A, 2B, and 2C.

Figure 1D:
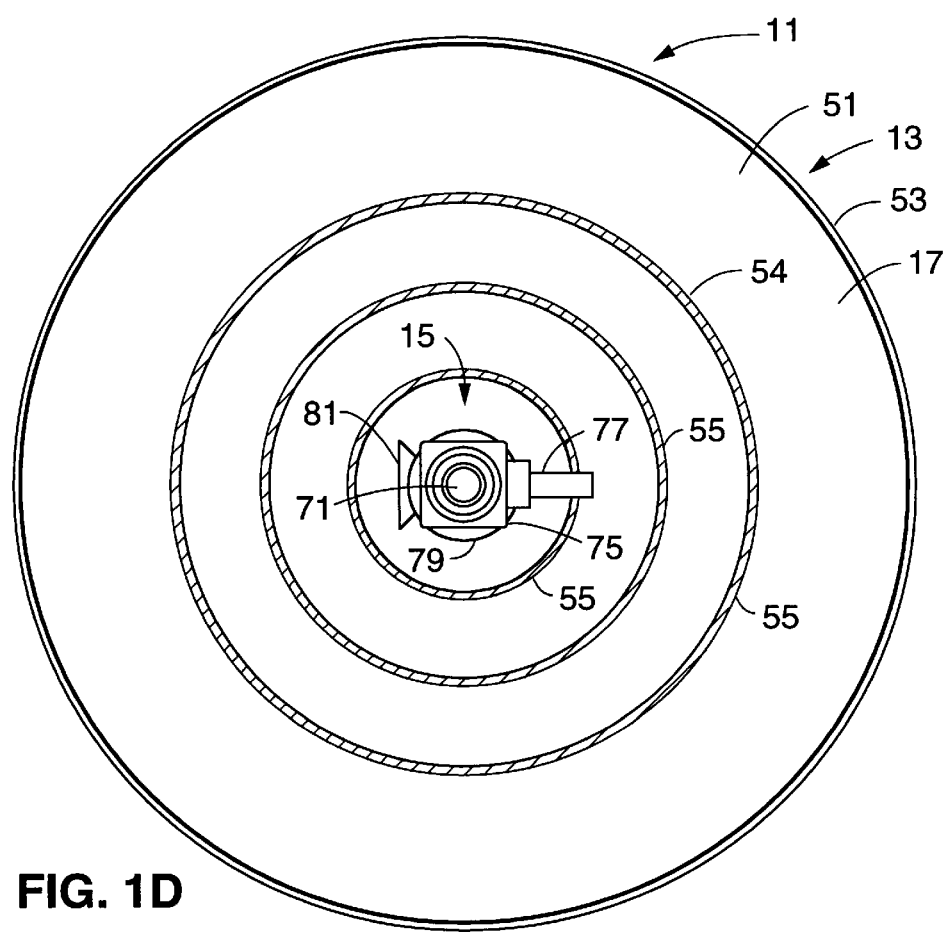
FIG. 1D is a top view of the first embodiment of the inflating lifting device according to the invention in its inflated state.

The external views in FIGS. 1A, 1C and 1D show the inflating lifting device 11 with the body wall engaging element 13 attached to the distal end of the lifting tube 15. The body wall engaging element includes the envelope 17.

In the packaged state 201 shown in FIG. 2A, the body wall engaging element forms a linear extension of the lifting tube 15, and is enclosed in the sheath 131, as will be described in more detail below. In its packaged state, the body wall engaging element 13 passes easily through a laparoscopic incision in the body wall into the underlying body cavity, for example, the abdominal cavity.

To minimize trauma to the patient, it is desirable that the laparoscopic incision be as small as possible. Consequently, it is desirable that the cross-sectional area of the packaged inflating lifting device 201 be as small as possible. The size of the incision required depends on the bulk of the body wall engaging element in its packaged state. However, the largest of the body wall engaging elements according to the invention require a laparoscopic incision less than 14 mm long.

Once the distal part of the packaged inflating lifting device 201 is inside the body cavity, an inflation fluid is passed into the body wall engaging element to inflate the body wall engaging element to the inflated state shown in FIGS. 1A–1D. In the expansion process, the body wall engaging element 13 expands laterally by a factor of about 150 (area) while its length decreases by a factor of about two.

After is has been inflated, the body wall engaging element 13 has the large, flat, lifting surface 14 by means of which it transfers the lifting force applied to the lifting tube 15 to the body wall. Despite the large area of the lifting surface, the height of the body wall engaging element in the axial direction is relatively small, typically in the range of 12–25 mm, which minimizes the intrusion of the inflated body wall engaging element into the working space created by lifting the body wall.

The large area of the lifting surface 14 of the body wall engaging element 13 enables a large area of the body wall to be lifted and distributes the lifting force applied to the lifting tube 15 uniformly over this large area. As a result, the maximum lifting pressure applied to the body wall is not significantly greater than that applied by convention gas insufflation.

Figure 3A:
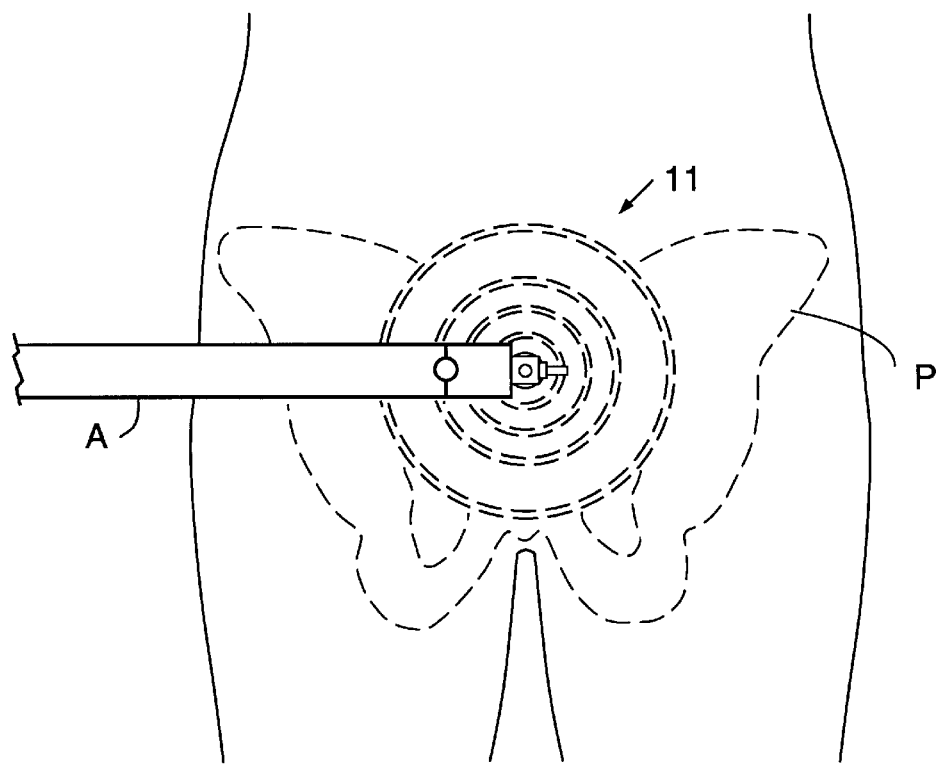
FIG. 3A is a plan view of the human abdomen showing how the first embodiment of the inflating lifting device in its inflated state fits within the bounds defined by the pelvis.

FIGS. 1A–1D show a version of the inflating lifting device 11 having the simple, circular body wall engaging element 13. This shape of body wall engaging element is suitable for lifting the wall of the lower abdomen. The circular shape of the body wall engaging element fits in the shape defined by the pelvis, as shown in FIG. 3A.

Figure 3B:
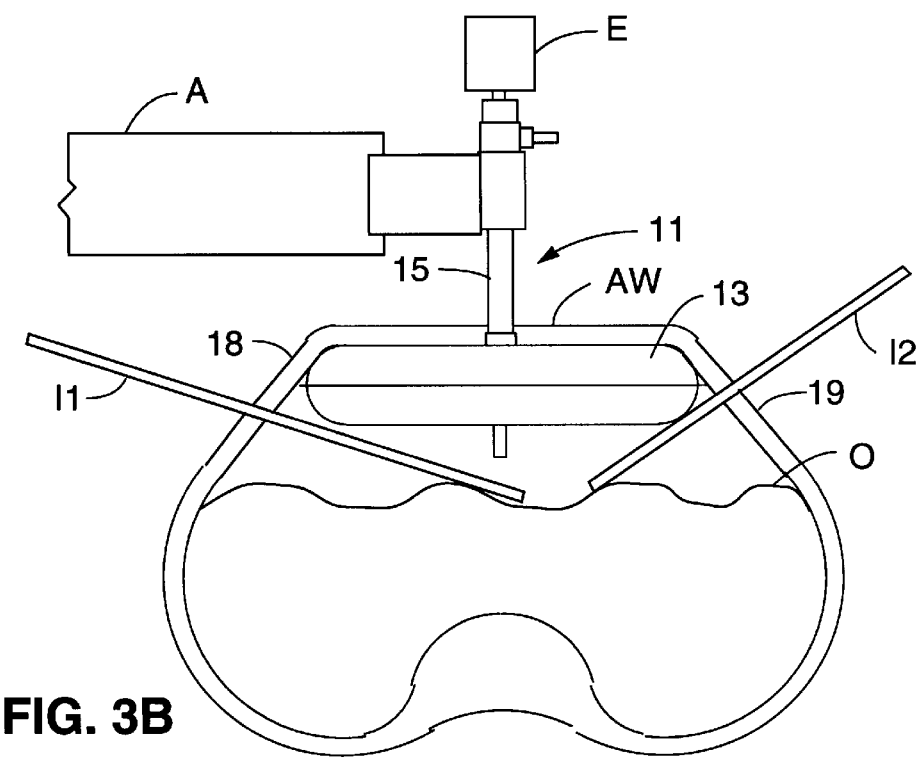
FIG. 3B is a transverse cross-sectional view of the human abdomen showing instruments inserted around the periphery of the body wall engaging element of the first embodiment of the inflating lifting device according to the invention.

FIG. 3B shows the abdominal wall AW lifted by the inflating lifting device 11 attached to the lifting arm A. The large area of the body wall engaging element 13 in contact with the abdominal wall obstructs, to some extent, access for instruments to treat the organs O underlying the lifted portion of the abdominal wall. However, an oblique access for instruments, such as the instruments $I_1$ and $I_2$ is available through the parts of the abdominal wall outside the periphery of the body wall engaging element. These parts of the abdominal wall are indicated by the reference numerals 18 and 19 in FIG. 3B. The bore of the lifting tube 15 provides an additional access for instruments, such as the endoscope E, as also shown in FIG. 3B, and as will be described in more detail below.

Figure 4A:
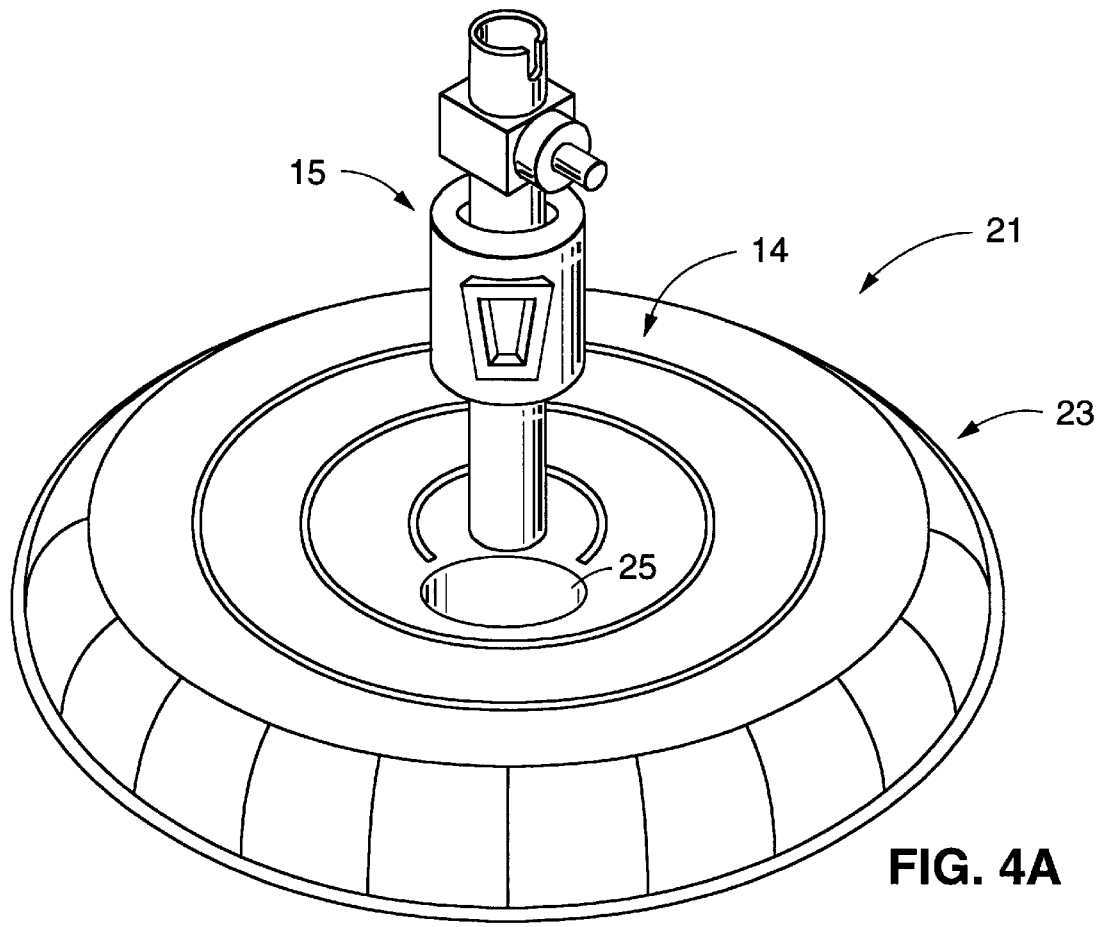
FIG. 4A is a perspective view of a second embodiment of the inflating lifting device according to the invention in its inflated state.
Figure 4B:
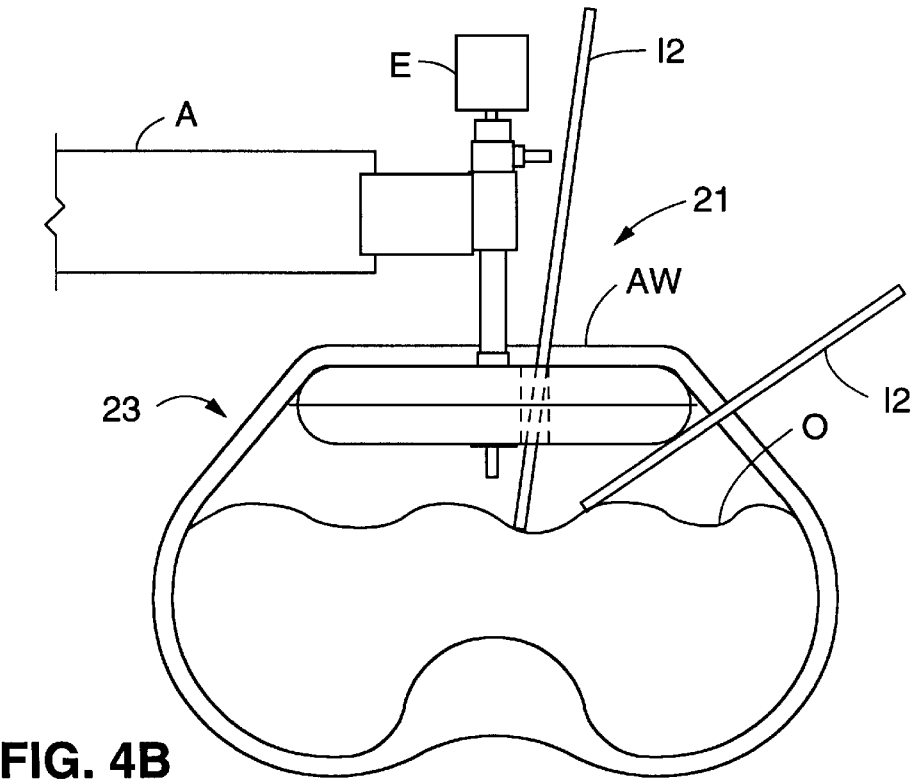
FIG. 4B is a transverse cross-sectional view of the human abdomen showing an instrument inserted through the instrument port in the body wall engaging element of the second embodiment of the inflating lifting device according to the invention.

If a less oblique access for instruments is required, the inflating lifting device 21 shown in FIG. 4A can be used. In this, the body wall engaging element 23 is formed with the access window 25 through which the instrument $I_1$ is passed, as shown in FIG. 4B. More than one access window can be provided if required.

Figure 5A:
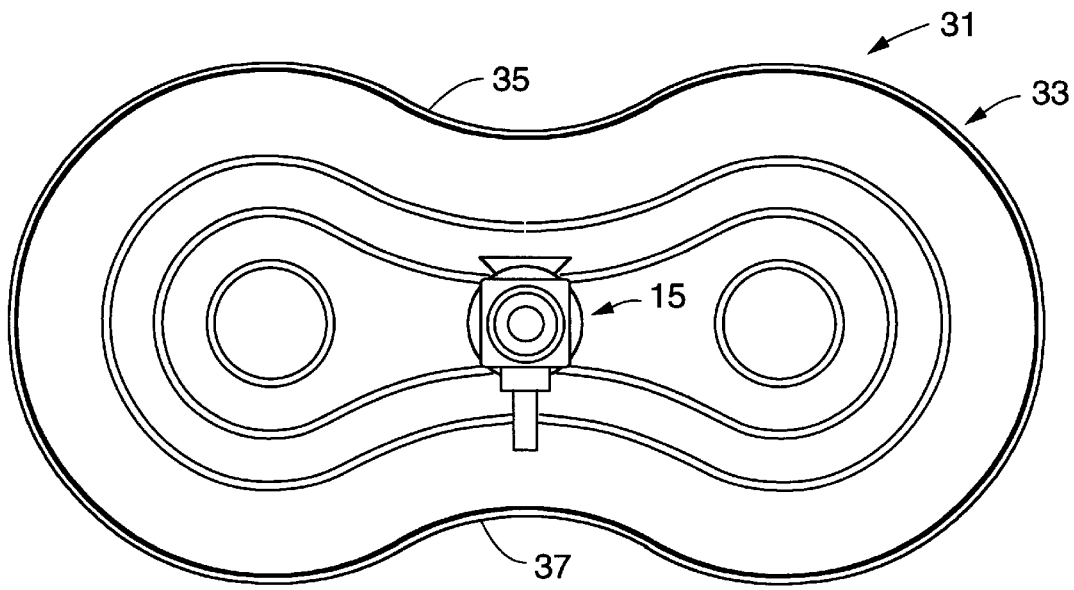
FIG. 5A is a plan view of a third embodiment of the inflating lifting device according to the invention in its inflated state.
Figure 5B:
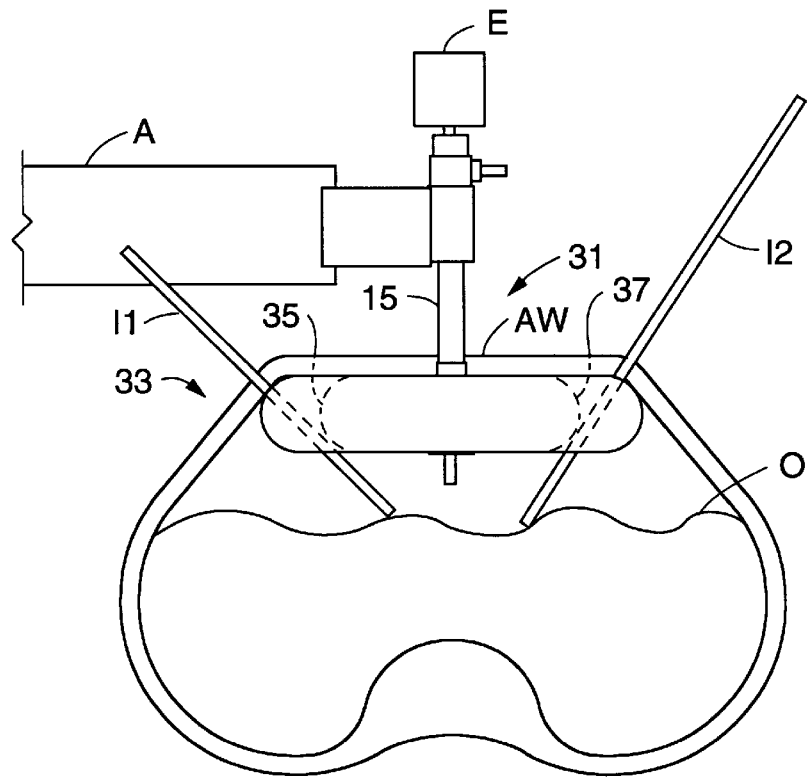
FIG. 5B is a transverse cross-sectional view of the human abdomen showing instruments inserted outside the waisted portion of the body wall engaging element of the third embodiment of the inflating lifting device according to the invention.

As an alternative to using the inflating lifting device 21 having a circular body wall engaging element 23 with the access window 25 shown in FIG. 4A, the inflating lifting device 31, shown in FIG. 5A, can be used. In this, the body wall engaging element 33 includes the concave waisted portions 35 and 37. As shown in FIG. 5B, the concave waisted portions allow instruments to pass outside the periphery of the body wall engaging element at a less oblique angle than that shown in FIG. 3B.

Figure 6A:
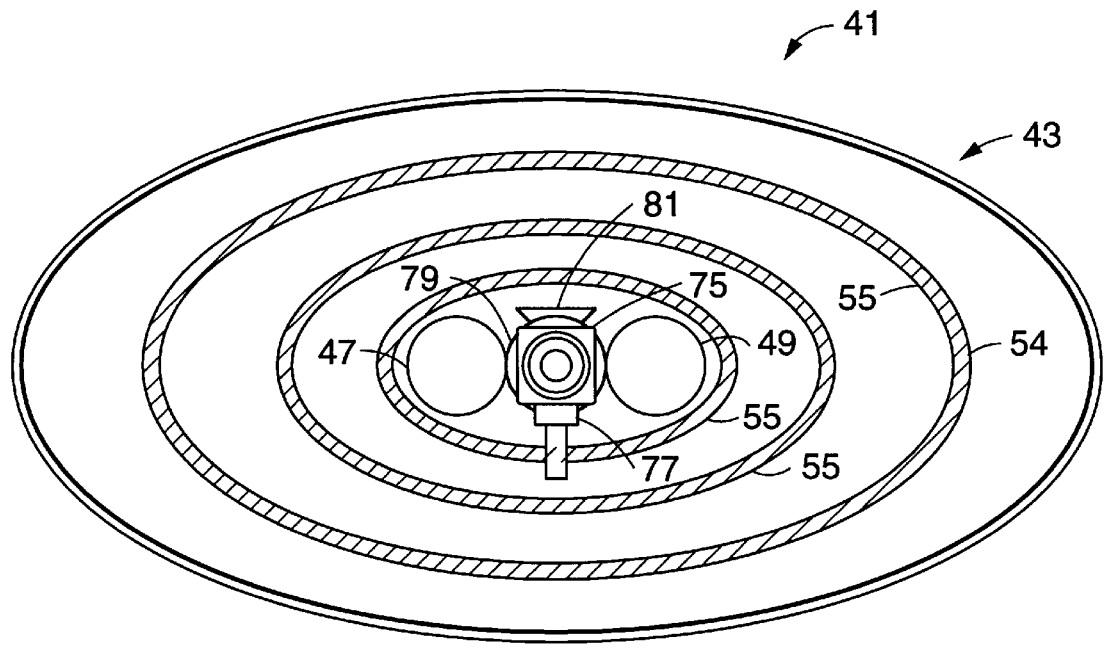
FIG. 6A is plan view of a fourth embodiment of the inflating lifting device according to the invention in its inflated state.
Figure 6B:
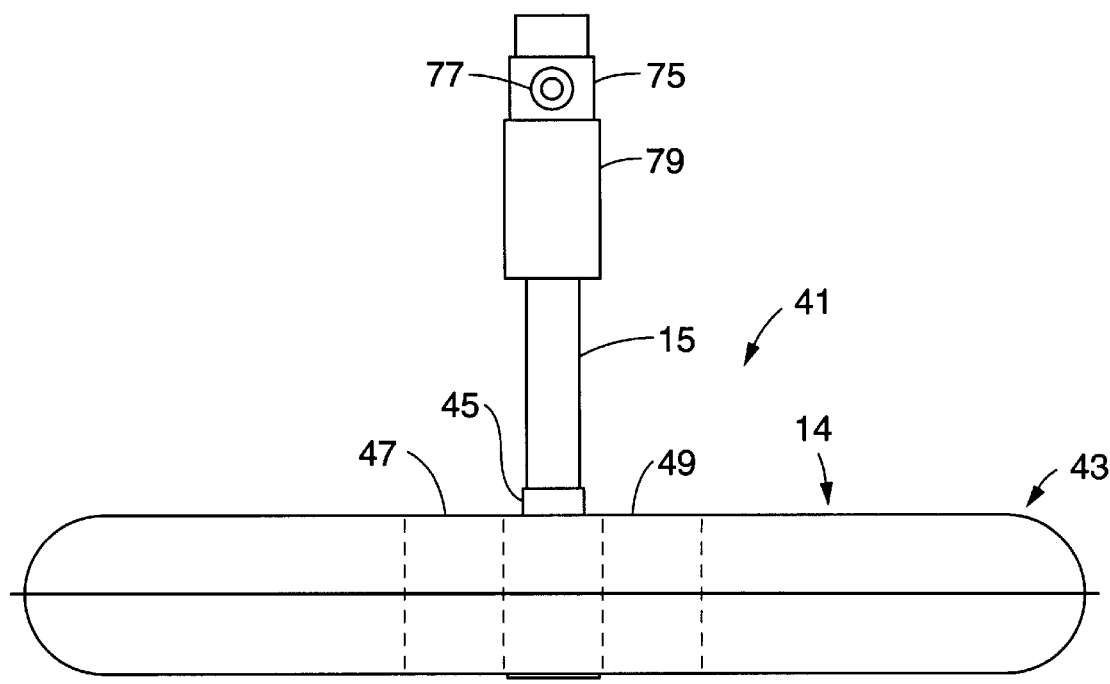
FIG. 6B is a side view of a fourth embodiment of the inflating lifting device according to the invention in its inflated state.

The inflating lifting device 41 shown in FIGS. 6A and 6B has an oval body wall engaging element 43, shaped to provide improved longitudinal lifting of the upper abdominal wall. The body wall engaging element 43 includes the two access windows 47 and 49 adjacent the lifting tube connection 45 to provide instrument access through the body wall engaging element 43.

Details of the construction of the body wall engaging element 13 of the inflating lifting device 11 are shown in FIGS. 1A–1D. The envelope 17 of the body wall contacting element is formed from the upper envelope half 51 and the lower envelope half 52. The envelope halves are shaped to define the shape of the body wall engaging element. Accordingly, in the circular body wall engaging element 13, the upper and lower envelope halves are substantially circular. The envelope halves are attached to one another at their peripheries 53, preferably by RF welding.

The baffles 55 interconnect the upper and lower envelope halves 51 and 52. The baffles provide the body wall engaging element 13 with its plane lifting surface 14 when the body wall engaging element is inflated. Without the baffles, the lifting surface would be convex, instead of plane. This would make the body wall engaging element much fatter, which would cause the body wall engaging element to get in the way during the treatment procedure. Moreover, a convex body wall engaging element would concentrate the lifting force in the vicinity of the lifting tube 15, which would give an undesirable increase in the maximum lifting pressure.

The position of the outer-most baffle 54 relative to the periphery 53 of the envelope halves is chosen to provide the body wall engaging element 13 with the rounded shoulder 56. The rounded shoulder helps the body wall engaging element conform to the shape assumed by the abdominal wall at the transition between the portion of the abdominal wall that supported by the inflating lifting apparatus and the portion that is not supported. This prevents the lifting pressure applied to the abdominal wall increasing at the periphery of the body wall engaging element.

When the body wall engaging element 13 is inflated to its inflated state, the baffles 55 provide the body wall engaging element with much of the stiffness by which the body wall engaging element uniformly transfers the lifting force from the lifting tube 15 to the large area of the body wall. The baffles are preferably attached to the envelope halves by RF welding, as will be described below.

In the preferred embodiment, the baffles 55 are arranged so that they run parallel to the periphery 53 of the body wall engaging element 13. This divides the body wall engaging element into a number of concentric chambers. To allow inflation fluid to pass freely from the lifting tube 15 to each of the chambers, the holes 65 are formed in the baffles.

Figure 1E:
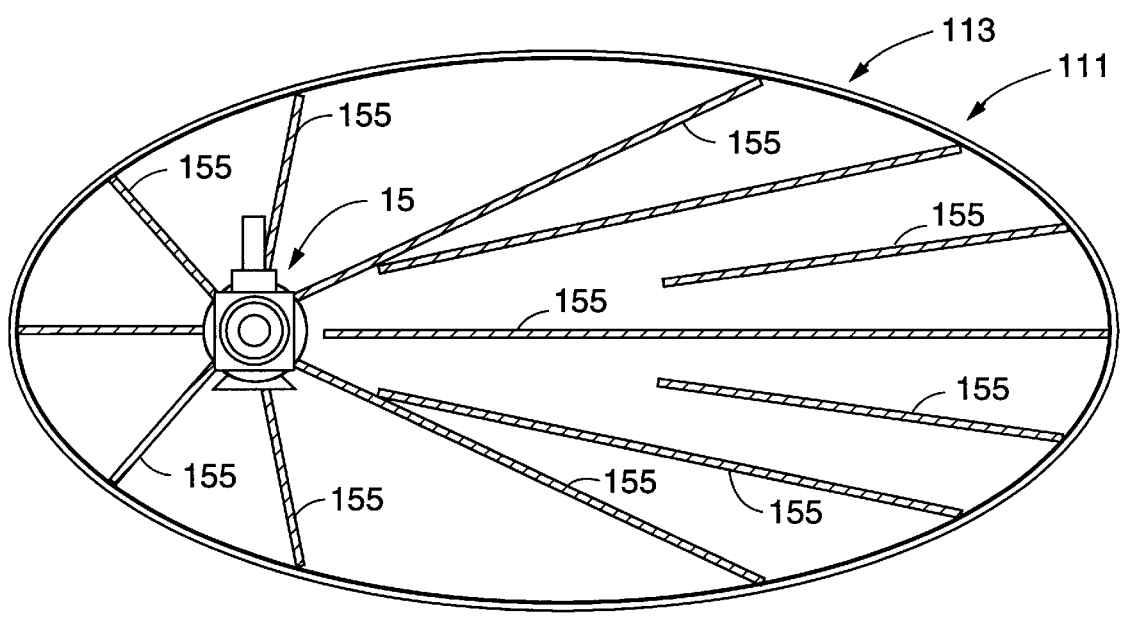
FIG. 1E is a top view of an alternative embodiment, having radial baffles, of the inflating lifting device according to the invention.

FIG. 1E shows an alternative embodiment in which the baffles 155 are arranged radially in the body wall engaging element 113 of the inflating lifting device 111. Radially-arranged baffles are advantageous in certain applications.

To provide the stiffness required to transfer the lifting force uniformly from the lifting tube 15 to the body wall, the body wall engaging element 13 must be capable of withstanding inflation pressures as high as 20 pounds per square inch. On the other hand, to minimize the bulk of the body wall engaging element in its packaged state, and, hence, to minimize the size of incision required, as thin a material as possible should be used for the envelope halves 51 and 52 and the baffles 55. Also, because of the stresses imposed by the inflation pressure on the attachment points between the envelope halves and the between the envelope halves and the baffles, the material of the envelope halves and the baffles must have good welding characteristics. Because of these requirements, the envelope halves and the baffles are preferably made of a composite film made by laminating a material with good welding characteristics, such as urethane, with a strong material, such as polyester. An alternative composite material is a composite film made by extruding a material with good welding characteristics, such as polyethylene, with a strong material, such as nylon.

In the preferred embodiment, a nylon or polyester fabric layer about 0.5 to 2 mil. (12–50 $\mu$m) thick is used as the core of the envelope material. The nylon or polyester fabric layer can be a woven fabric or can be a layer of randomly-oriented fibres. The nylon or polyester fabric layer is laminated between two polyurethane films to provide a film of envelope material with a preferred thickness of about 3 mil. (75 μm). The polyurethane films bond securely to the uneven surface of the nylon or polyester fabric layer.

The baffles 55 are preferably fabricated and attached to the upper envelope half 51 and the lower envelope half 52 by the process shown in FIGS. 7A through 7E. This process assembles the baffles and attaches them to the upper and lower envelope halves using two welding operations. The two-piece baffle used in the procedure saves having to bend the baffles prior to welding, as would be required if one-piece baffles were used. In the following example, the assembly of the circular body wall engaging element 13 shown in FIGS. 1A–1D will be described.

Each baffle is made from the annular upper baffle half 101 and the annular lower baffle half 103. One of the baffle halves, for example, the lower baffle half 103 is selectively coated with a suitable welding release agent in the shaded area 105 shown in FIG. 7A. The upper baffle half 101 is then laid on top of the lower baffle half 103, as shown in FIG. 7B, and the pair of baffle halves is placed between the first pair of circular RF welding electrodes $W_1$ and $W_1'$, as shown in the cross sectional view of FIG. 7C. The first welding electrodes $W_1$ and $W_1'$ then weld the two baffle halves together along their outer peripheries, as indicated by the phantom line 107 shown in FIG. 7B, to form the baffle 55.

The completed baffle 55 is then laid on the lower envelope half 52 between the circular second welding electrodes $W_2$ and $W_2'$, as shown in the cross-sectional view of FIG. 7D. The second welding electrodes have a smaller diameter than that of the first welding electrodes $W_1$ and $W_1'$. The upper envelope half 51 is then laid over the completed baffle and the lower envelope half. The second welding electrodes $W_2$ and $W_2'$ then perform a second welding operation to weld the baffle 55 along the inner periphery the baffle to the upper envelope half and the lower envelope half. For example, the second welding operation welds the upper baffle half 101 to the upper envelope half 51 along the phantom line 111, remote from the phantom line 107, shown in FIG. 7B.

The second welding operation welds the upper baffle half 101 to the upper envelope half 51, and welds the lower baffle half 103 to the lower envelope half 52. However, because of the welding release agent 105 between the two baffle halves in the region of the second weld, the second welding operation does not weld the baffle halves together. Accordingly, when the body wall engaging element is inflated, as shown in the cross-sectional view of FIG. 7E, part of the baffle welded to the lower envelope half 52 separates from the part of the baffle welded to the upper envelope half 51 until the baffles 55 are fully extended. The baffle halves 101 and 103 separate from one another except where they were welded along the line 107 (FIG. 7B) in the first welding operation.

In an actual assembly operation, plural completed baffles 55 would be placed on a lower envelope half 52 and an upper envelope half 51 would be placed over the baffles. This assembly would be placed between plural concentric circular (in the case of circular baffles) welding electrodes, one per baffle, and all the baffles would be attached to the upper and lower envelope halves in a single welding operation. An additional concentric welding electrode could be provided to weld the peripheries 53 (FIG. 1B) of the upper and lower envelope halves together in the same operation.

A process similar to that just described can be used to make other shapes of the body wall engaging element, for example, the body wall engaging elements 33 and 43 respectively shown in FIGS. 5A and 6A. The shape of the baffle halves, and the shape of the welding electrodes is changed according to the shape of the body wall engaging element.

Details of the lifting tube 15 are shown in FIG. 1B. The lifting tube 15 is a coaxial, double tube having an inner tube 67 concentric with the outer tube 69. The bore 71 of the inner tube provides access though the inflating lifting device for instruments, etc., as described above. The port 75 is mounted on the proximal end of the lifting tube. The port 75 includes the valve 77 through which inflation fluid can pass into and out of the body wall engaging element 13 via the lumen 73 between the inner tube and the outer tube of the lifting tube.

The upper envelope half 51 includes the lifting tube mounting hole 57. The upper lifting tube mounting 61 is inserted through the lifting tube mounting hole 57, and the flange 62 is attached to the inside of the upper envelope half concentrically with the lifting tube mounting hole 57, preferably by RF welding. The lower envelope half 52 includes the lifting tube mounting hole 59. The lower lifting tube mounting 63 is inserted through the lifting tube mounting hole 59, and the flange 64 is attached to the outside of the lower envelope half concentrically with the lifting tube mounting hole 59, preferably by RF welding. The upper and lower lifting tube mountings 61 and 63 are preferably urethane moldings.

The lifting tube 15 is passed through the upper lifting tube mounting 61 and is advanced until the inner tube 67 engages with the lower lifting tube mounting 63 and the outer tube 69 engages with the upper lifting tube mounting 61. The inner tube and the outer tube are respectively attached to the lower and upper lifting tube mountings using a suitable adhesive. In the preferred embodiment, a flexible UV-curable adhesive is used.

The lifting adaptor 79 is mounted on the lifting tube 15 and abuts against the port 75. The lifting adaptor can slide axially along the lifting tube, and the lifting tube can rotate relative to the lifting adaptor. The lifting adaptor connects the inflating lifting device 11 to the lifting arm A (see FIGS. 3B, 4B, 5B), which provides the lifting force in the lifting direction, i.e., the direction that raises the body wall.

The lifting adaptor 79 and the lifting arm A preferably include the mating halves of a unidirectional coupling, such as the dovetail connector 81 by means of which the lifting adaptor is attached to the lifting arm. The unidirectional coupling prevents the lifting arm from applying a force to the inflating lifting device 11 in the direction opposite to the lifting direction. If the lifting arm is lowered too far, the unidirectional coupling disengages to prevent the lifting arm from driving the inflating lifting device into the body cavity, thereby preventing trauma to the organs underlying the lifting site. The sliding mounting of the lifting adaptor 79 on the lifting tube 15 provides a further degree of protection against inadvertent application of a reverse lifting force to the lifting tube.

As an alternative to using the lifting arm A, the surgeon may grip the lifting adaptor 79 and the port 75 by hand and manually apply the lifting force to the inflating lifting apparatus 11 to lift the body wall. The lifting adaptor 79 may be shaped to provide a gripping surface to facilitate such manual operation. As a further alternative, the lifting adaptor 79 may be omitted, and the port 75 and/or the proximal part of the lifting tube 15 may be shaped to provide a gripping surface for manual operation.

Figure 8A:
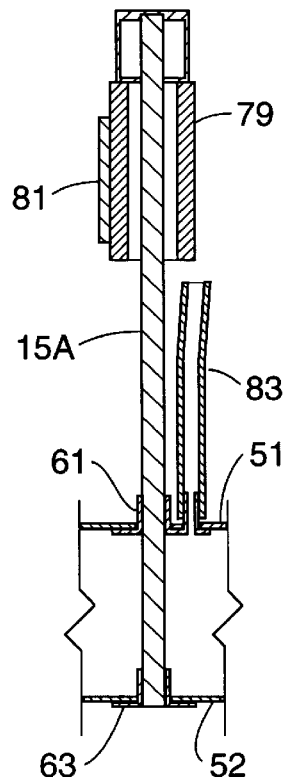
FIG. 8A is a cross-sectional view showing a first alternative embodiment of the lifting tube of the inflating lifting device according to the invention.

A number of alternative embodiments of lifting tube 15 are shown in FIGS. 8A–8D. FIG. 8A shows the solid lifting tube 15A, which is attached to both the upper envelope half 51 and the lower envelope half 52, as described above. Making the lifting tube solid allows the diameter of the lifting tube to be reduced. Inflation fluid is passed into and out of the body wall engaging element 13 via the independent inflation tube 83. The separate inflation tube may optionally be attached to the lifting tube 15A. The solid lifting tube may alternatively be attached to the upper envelope half only, instead of to both the upper and lower envelope halves, in a manner similar to that shown in FIG. 8D.

Figure 8B:
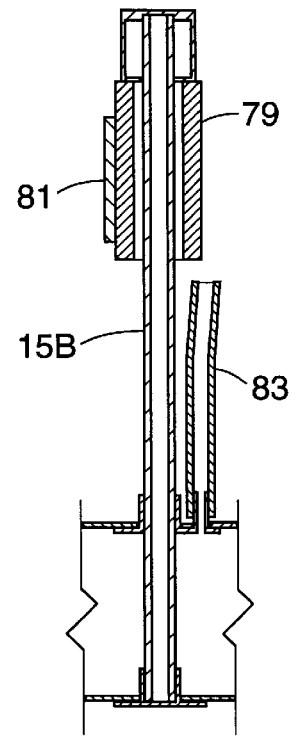
FIG. 8B is a cross-sectional view showing a second alternative embodiment of the lifting tube of the inflating lifting device according to the invention.

In FIG. 8B, the lifting tube 15B is a single hollow tube, and inflation fluid is passed into and out of the body wall engaging element 13 using the independent inflation tube 83. The hollow lifting tube 15B provides access for instruments to the organs directly underlying the body wall engaging element.

Figure 8C:
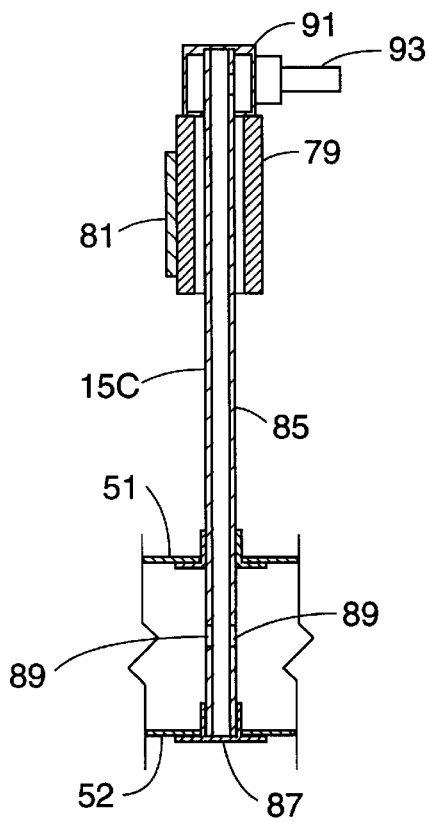
FIG. 8C is a cross-sectional view showing a third alternative embodiment of the lifting tube of the inflating lifting device according to the invention.

In FIG. 8C, the lifting tube 15C is a single hollow tube 85 having a closed distal end 87. The tube 85 is attached to both the upper envelope half 51 and the lower envelope half 52, as described above. Radial ports 89 are provided in the tube 85 near the closed distal end. The proximal end of the lifting tube is fitted with the port 91, which includes the valve 93. Inflation fluid passes from the valve 93, through the bore of the tube 85 and the radial ports 89, into the body wall engaging element 13. The port 91 may optionally include a flap valve (not shown) in its proximal face to maintain the inflation pressure in the tube 85 while allowing an endoscope to be passed into the bore of the tube 85 to view through the closed distal end 87.

Figure 8D:
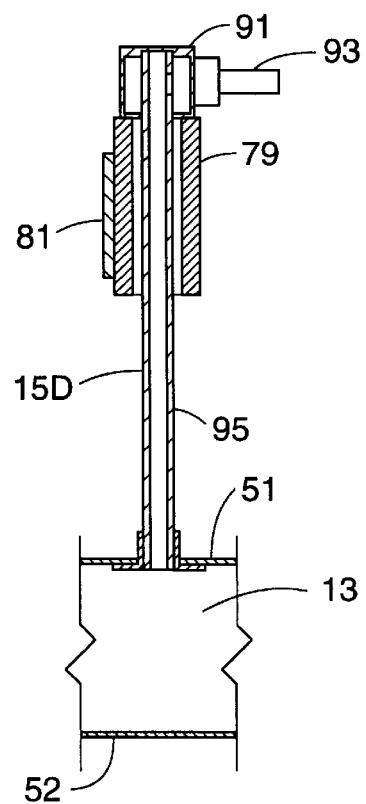
FIG. 8D is a cross-sectional view showing a fourth alternative embodiment of the lifting tube of the inflating lifting device according to the invention.

In FIG. 8D, the lifting tube 15D is a single hollow tube 95 having an open distal end. The tube 95 is attached only to the upper envelope half in the manner described above. The proximal end of the lifting tube is fitted with the port 91, which includes the valve 93. Inflation fluid passes from the valve 93, through the bore of the tube 95, and into the body wall engaging element 13. The port 91 may optionally include a flap valve (not shown) in its proximal face to maintain the inflation pressure in the tube 95 while allowing an endoscope to be passed into the bore of the tube 95 to view through the lower envelope half 52.

Figure 9:
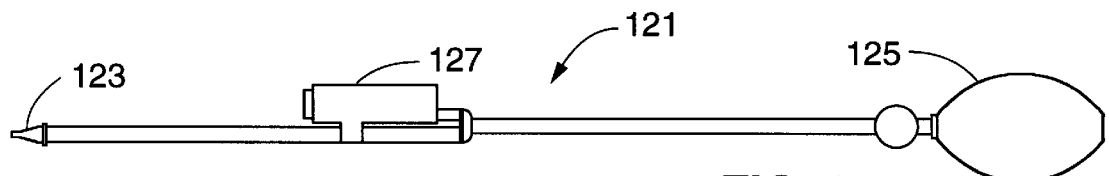
FIG. 9 is a side view of the inflating apparatus.

The body wall engaging element 13 is preferably inflated by connecting the inflation apparatus 121 shown in FIG. 9 to the valve, such as the valve 77 shown in FIGS. 1A–1D, on the inflating lifting apparatus 11. In the inflation apparatus 121, the connector 123 is shaped to connect to the valve on the inflating lifting apparatus, and the inflation fluid is air, pressurized by manually operating the bulb 125. The pressure gauge 127 is provided to enable the surgeon to monitor the pressure in the body wall engaging element.

The valve, such as the valve 77, fitted to the inflating lifting device 11 is preferably a one-way valve that maintains the inflation pressure in the body wall engaging element 13 when the connector 123 is disconnected from the valve.

The valve 77 is also preferably a pressure control valve. When the lifting force is applied to the inflating lifting apparatus 11, and the body wall engaging element 13 transfers this lifting force to the body wall, some deformation of the body wall engaging element occurs. This deformation can reduce the volume of the body wall engaging element, which causes the pressure in the inflating lifting device to rise. Using a pressure control valve as the valve 77 prevents the pressure in the inflating lifting device from rising to a level that could compromise reliability. A pressure control valve bleeds off inflation fluid from the inflating lifting device when the pressure in the inflating lifting device exceeds the pressure setting of the valve. The pressure setting of the pressure control valve is chosen to be below the pressure that could compromise the reliability of the inflating lifting device.

The inflating lifting apparatus is shown in its packaged state 201, prior to deployment in FIGS. 2A and 2B. To package the inflating lifting device after assembly, the body wall engaging element 13 is evacuated, and the periphery 53 (FIG. 1A) of the envelope 17 is gathered together and is drawn distally until the envelope 17 forms an axial extension of the lifting tube 15. The envelope 17, indicated by the shaded area in FIG. 2B, is then compacted radially, and is inserted into the sleeve 131. The sleeve maintains the device in its packaged state 201.

The sleeve 131 is an elongate bag of a suitable material, such as polyethylene. The sleeve covers the packaged envelope 17, and extends up the outside of the lifting tube 15, towards the port 75, as shown in FIGS. 2A and 2B.

The sleeve 131 is formed with the longitudinal perforations 133 over the portion of its length that covers the envelope 17. The body wall engaging element 13 is released from its packaged state as follows. After the distal part of the inflating lifting device 11 has been inserted into the body cavity, as will be described below, inflation fluid is passed into the body wall engaging element 13. The resulting expansion of the body wall engaging element ruptures the sleeve 131 over the distal part of its length, along the perforations 133. The ruptured sleeve no longer retains the envelope 17 in its packaged state, and additional inflation fluid will then expand the body wall engaging element to its fully inflated state.

The inflated body wall engaging element retains the used sleeve in position on the lifting tube 15. Withdrawing the inflating lifting apparatus 11 at the end of the treatment procedure then automatically removes the used sleeve from the body cavity.

The sleeve 131A may alternatively be formed with the longitudinal slit 135 over its entire length, as shown in FIG. 2C. Opposite edges of the slit 135 are held together by the detachable lacing 137, or by a tear strip (not shown). The proximal end 139 of the detachable lacing is temporarily attached to the port 75 or to some other proximal point on the packaged apparatus 201A. The sleeve includes the proximal extension 141 to enable the used sleeve to be withdrawn from the body cavity after the body wall engaging element has been deployed.

After the distal end of the packaged inflating lifting device 201A has been inserted into the body cavity, as will be described in more detail below, the proximal end 139 of the detachable lacing is released from the port 75, and is pulled proximally to release the detachable lacing from the sleeve 131A. The detachable lacing is pulled until it is completely withdrawn from the body cavity. This releases the sleeve 131 from around the packaged envelope 17. The proximal extension 141 is then pulled proximally to withdraw the used sleeve 131A from the body cavity. Inflation fluid is then passed through the valve 77 to inflate the body wall engaging element.

Figure 2D:
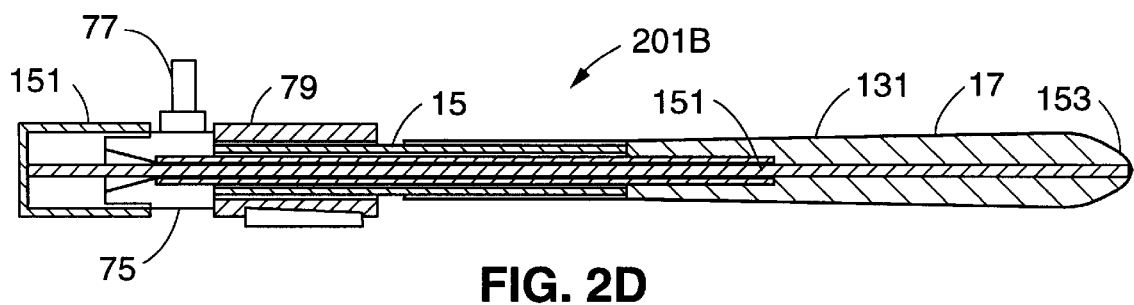
FIG. 2D is a cross-sectional view of the first embodiment of the inflating lifting device according to the invention in its packaged state in which a blunt-tipped trocar is included in the packaged device.

The packaged inflating lifting device 201 has sufficient axial stiffness to enable it to be inserted into a body cavity through an incision in the body wall. If the packaged inflating lifting device is additionally to be used to perform blunt dissection, an increased axial stiffness may be required. The axial stiffness of the packaged inflating lifting apparatus may be increased by inserting the blunt-tipped trocar 151 into the lifting tube 15 prior to packaging the inflating lifting device, as shown in FIG. 2D. The blunt-tipped trocar projects beyond the end of the lifting tube. The envelope 17 is then wrapped around the outside of the blunt-tipped trocar and is retained in position by the sleeve 131 as described above. The length of the blunt-tipped trocar is chosen so that the distal tip of the trocar projects beyond the end of the wrapped envelope 17. The sleeve 131 covers the distal tip of the blunt-tipped trocar, and the distal tip of the trocar and the sleeve together provide the packaged device with the smooth, hard, rounded nose 153 that can be used to perform blunt dissection. The blunt-tipped trocar 151 is removed from the packaged apparatus after the sleeve 131 has been ruptured.

The inflating lifting device is used to lift a body wall according to the following method. A method for lifting the lower abdominal wall using the inflating lifting apparatus with the circular body wall engaging element shown in FIGS. 1A–1D will be described as an example. The method described can readily be adapted to lift other body walls using an inflating lifting device with the same-shaped or a different-shaped body wall engaging element.

Figure 10A:
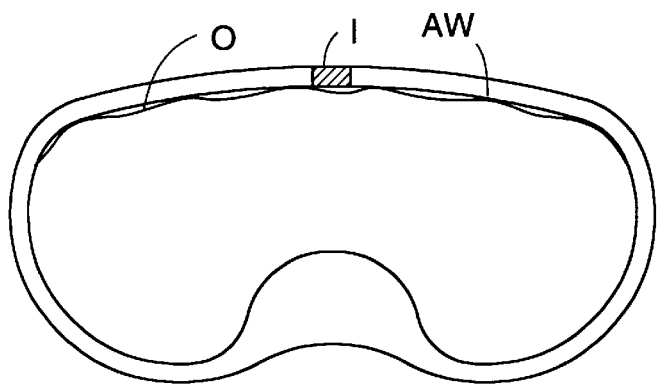
FIGS. 10A–10H are transverse cross-sectional views of the human abdomen illustrating methods according to the invention of using the first embodiment of the inflating lifting device according to the invention to lift the abdominal wall.
Figure 10B:
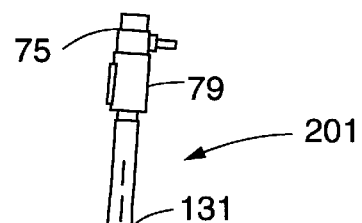
Figure 10B:
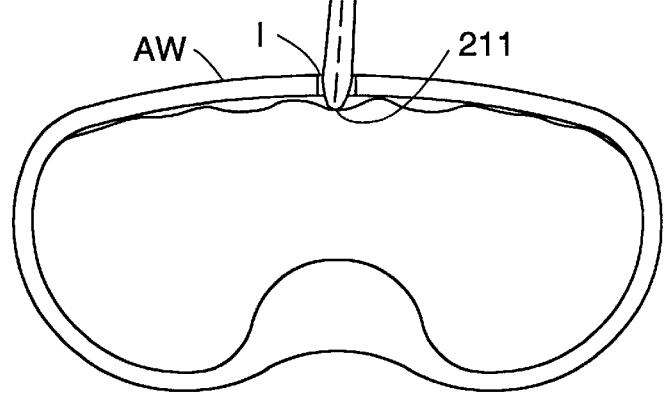

The lifting site is defined according to the treatment procedure that will follow the lifting. The center of the lifting site is then determined and a laparoscopic incision I is made through the abdominal wall AW, as shown in FIG. 10A. The laparoscopic incision is normally between 10 and 12 mm long, and, in any case, is less than 14 mm long. The proximal end of the packaged inflating lifting apparatus 201 is grasped, and its distal tip 211 is then inserted into the incision, as shown in FIG. 10B.

Figure 10C:
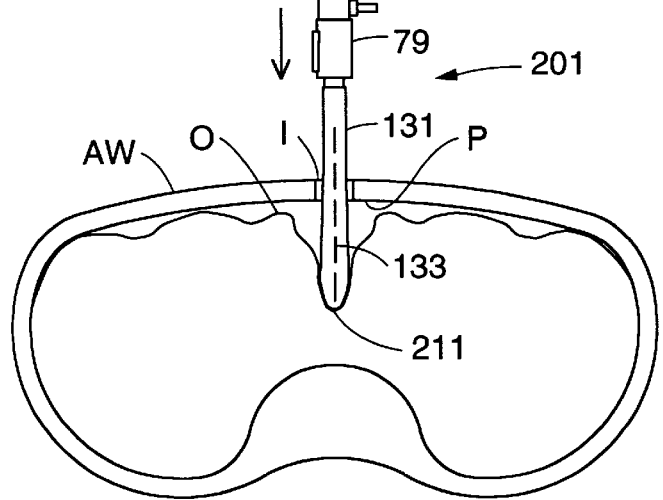

The packaged inflating lifting device is then advanced through the abdominal wall until the point of attachment between the upper envelope half 51 and the lifting tube 15 (FIGS. 1A–1D) pass through the peritoneum P on the inner surface of the abdominal wall, as shown in FIG. 10C. This can be judged by observing depth marks 203 printed on the sleeve 131, as shown in FIG. 2A. As the packaged inflating lifting apparatus 201 is advanced through the abdominal wall, the blunt, rounded distal tip 211 gently displaces the underlying viscera O downwards, away from the abdominal wall, and sideways, also as shown in FIG. 10C.

Figure 10D:
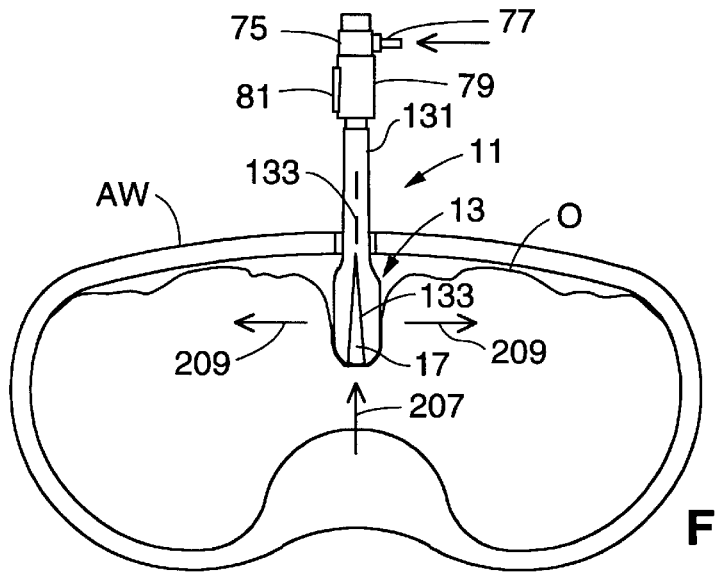

The inflating apparatus 121 (FIG. 9) is then connected to the valve 77, and the bulb 125 is squeezed to feed inflation fluid into the body wall engaging element 13, as indicated by the arrow 205. The resulting expansion of the body wall engaging element ruptures the sleeve 131 along the perforations 133, which releases the envelope 17 from its packaged state, as shown in FIG. 10D. Release of the envelope can be sensed by an abrupt drop in the resistance to squeezing the bulb.

The bulb 125 is then squeezed an additional number of times to feed more inflation fluid into the body wall engaging element 13. This inflates the body wall engaging element. As the body wall engaging element inflates it shortens axially, as shown by the arrow 207, and spreads laterally, as shown by the arrow 209. The movement of the body wall engaging element keeps the viscera O out of the contact area between the body wall engaging element and the abdominal wall. The pressure gauge 127 (FIG. 9) is monitored during the inflation operation, and the inflation operation is stopped when the recommended inflation pressure is reached. The recommended inflation pressure is high enough to provide the required degree of stiffness in the body wall engaging element, but is not so high as to compromise the reliability of the inflating lifting device. The inflation apparatus is disconnected from the valve 77 at the end of the inflation operation.

Figure 10E:
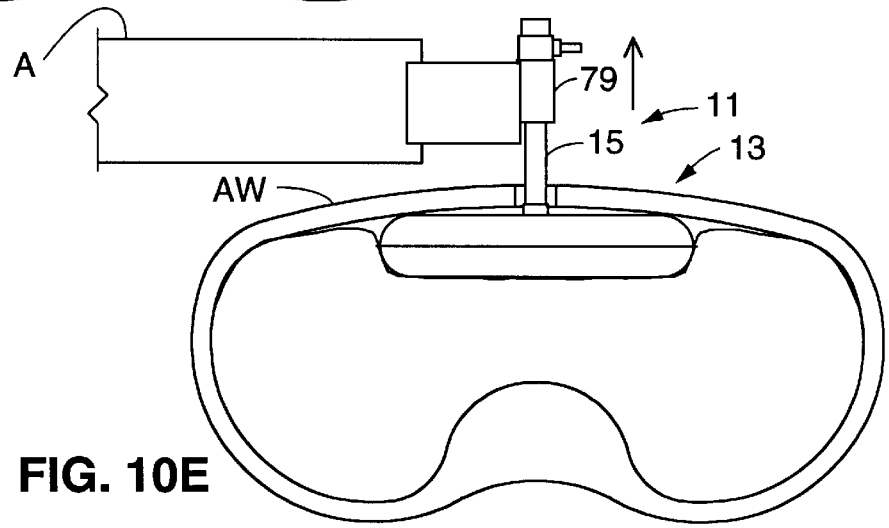
Figure 10F:
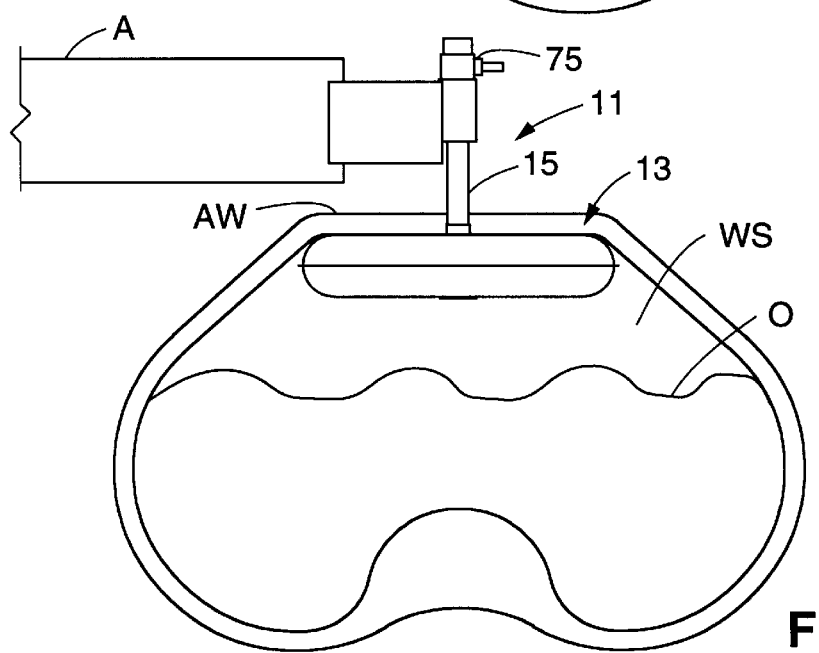

When the body wall engaging element is in its fully inflated state, the lifting adaptor 79 is attached to the lifting arm A using the dovetail connector 81, as shown in FIG. 10E. In FIGS. 10E and 10F, the used sleeve 131 is not shown in position around the lifting tube 15, for clarity. Raising the lifting arm A applies a lifting force to the lifting adaptor, and thence, via the port 75 and the lifting tube 15, to the body wall engaging element 13. The body wall engaging element applies the lifting force to a large area of the abdominal wall, which raises the abdominal wall to the position shown in FIG. 10F. The working space WS is formed between the underside of the inflating lifting device 11 and the underlying organs O.

During the lifting operation, the body wall engaging element 13 may deform. If, as a result, the inflation pressure in the inflating lifting device 11 increases to a level approaching that which could compromise the reliability of the device, the valve 75 releases inflation fluid from the apparatus. This prevents the inflation pressure from increasing further, and maintains the reliability of the inflating lifting device.

Before, during, or after the raising operation, an endoscope E can be inserted into the lifting tube 15 to observe the underlying organs, as shown, for example, in FIG. 3B. The endoscope can be left in position during the treatment procedure that follows, or can be replaced by one or more surgical instruments. Additional instruments can be inserted through trocar tubes driven through the abdominal wall outside the periphery of the body wall engaging element, also as shown in FIG. 3B. In addition, trocar tubes can be driven through the abdominal wall and further through the tool ports in the body wall engaging element, as shown in FIG. 4B.

One possible way of using the tool port is to insert a pneumoneedle through the part of the body wall known to overly the tool port. An endoscope is used to confirm that the puncture in the body wall lies in the center of the tool port. Then, the pneumoneedle is removed and a trocar is driven through the body wall at the site of the pneumoneedle puncture, and is advanced through the tool port. The trocar is then removed from the trocar tube, and instruments are passed into the working space underlying the inflating lifting device through the trocar tube in the instrument port. The trocar tube is omitted from FIG. 4B for clarity.

At the end of the treatment procedure, the lifting arm A is lowered to restore the abdominal wall AW to its original (non-lifted) state. During the lowering process, the sliding mounting of the lifting adaptor 79 on the lifting tube 15, and the unidirectional connection 81 between the lifting arm A and the lifting adaptor 79 minimize the risk of the lifting arm applying a downwards force to the organs underlying the inflating lifting device. Even if a downwards force is nevertheless inadvertently applied to the inflating lifting apparatus, the large surface area of the body wall engaging element 13 minimizes the resulting pressure applied to the underlying organs.

The inflating lifting device 11 is disconnected from the lifting arm A, and the inflating apparatus 121 (FIG. 9) is reconnected to the valve 77 to release the inflation fluid from the body wall engaging element 13. The valve 77 is then connected to a source of suction to evacuate the body wall engaging element. After the body wall engaging element is fully evacuated, the lifting tube 15 is manipulated to withdraw it from the incision I. This, in turn, withdraws the collapsed body wall engaging element 13 and the used sleeve 131 from the abdominal cavity. The incision is then closed to finish the procedure.

Figure 10G:
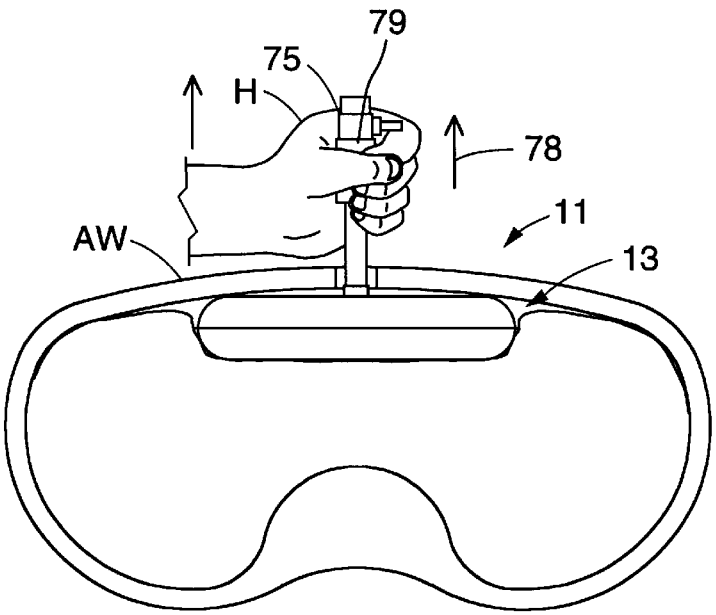
Figure 10H:
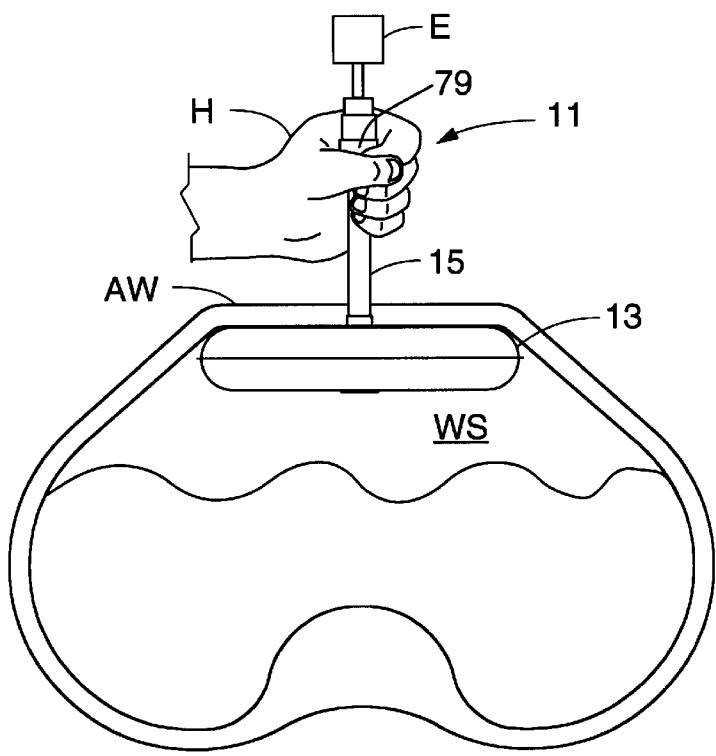

The inflating lifting device 11 may be used to lift a body wall manually, as illustrated in FIGS. 10G and 10H. The body wall engaging element 13 is deployed under the body wall using the procedure described above with reference to FIGS. 10A–10D. Then, when the body wall engaging element is fully inflated, instead of connecting the lifting adaptor 79 to the lifting arm, the surgeon grips the lifting adaptor 79 and part of the port 75, as shown in FIG. 10G. The surgeon then applies a lifting force to the inflating lifting device in the direction shown by the arrow 78 in FIG. 10G. This raises the abdominal wall as shown in FIG. 10H. The endoscope E can then be inserted into the bore of the lifting tube 15 to provide viewing of the working space WS. As mentioned above, the lifting adaptor and/or the port and/or the proximal part of the lifting tube can be shaped to provide a gripping area to facilitate manual lifting.

It is envisaged that the manual lifting technique just described will be used especially in emergency rooms and trauma centers to lift relatively small areas of body walls to provide short-term observation of the underlying organs.

Figure 11A:
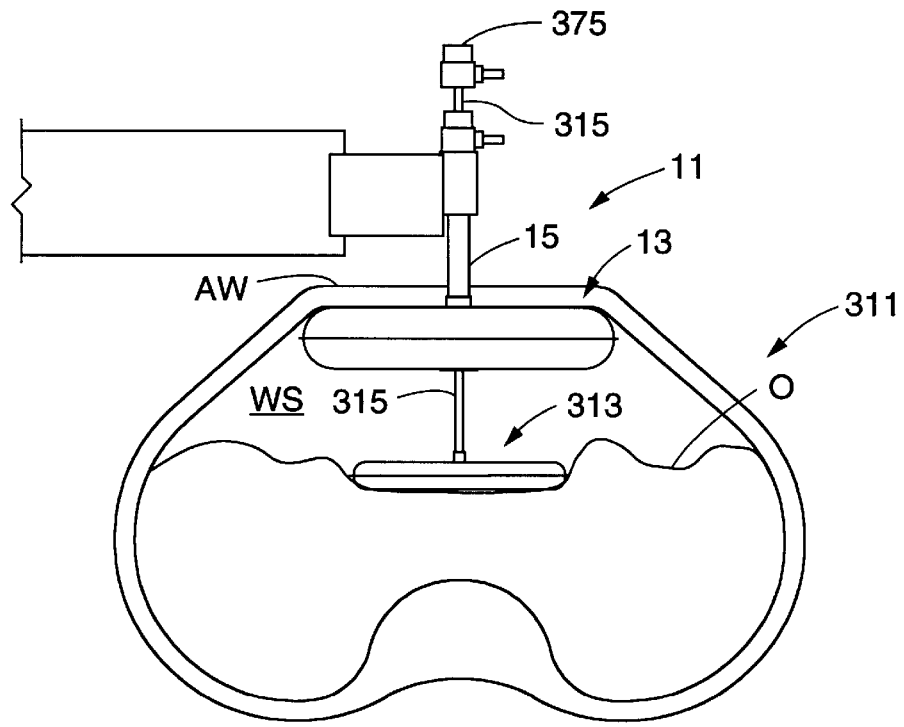
FIG. 11A is a transverse cross-sectional view of the human abdomen showing the auxiliary retractor according to the invention operating together with the inflating lifting device according to the invention. In this Figure, the abdominal wall has been raised using a mechanical lifting arm.

In some procedures, it is necessary to retract organs or tissue underlying the body wall to prevent them from obstructing access to the tissue to be treated. FIGS. 11A–11D show the auxiliary retractor 311 that operates together with the inflating lifting apparatus 11 to provide such retraction. FIG. 11A shows the auxiliary retractor 311 deployed together with the inflating lifting apparatus 11. After the inflating lifting apparatus 11 has raised the body wall (the abdominal wall is shown as an example) to create the working space, the auxiliary retractor in its packaged state is introduced into the working space WS through the bore of the lifting tube 15. The retraction element 313 is then inflated as shown, and the auxiliary retractor is slid distally to retract the organs O underlying the inflating lifting apparatus.

Figure 11B:
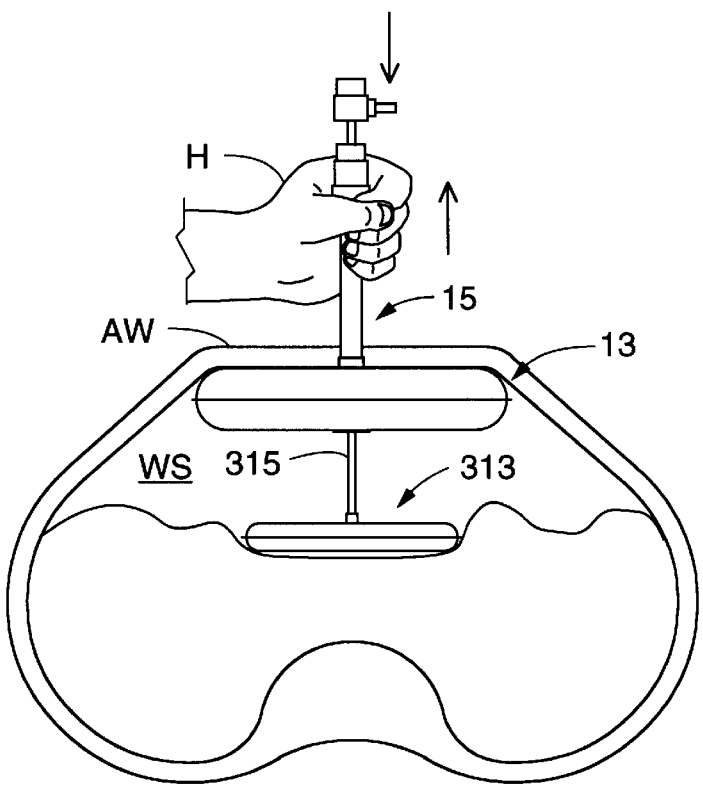
FIG. 11B is a transverse cross-sectional view of the human abdomen showing the auxiliary retractor according to the invention used together with the inflating lifting device according to the invention. In this Figure, the surgeon has raised the abdominal wall manually.

FIG. 11B shows the auxiliary retractor 313 operating together with the inflating lifting apparatus 11 when the latter is used manually to raise the body wall AW. The lifting force is applied to the inflating lifting device by the surgeon's hand H gripping the proximal part of the device.

Figure 11C:
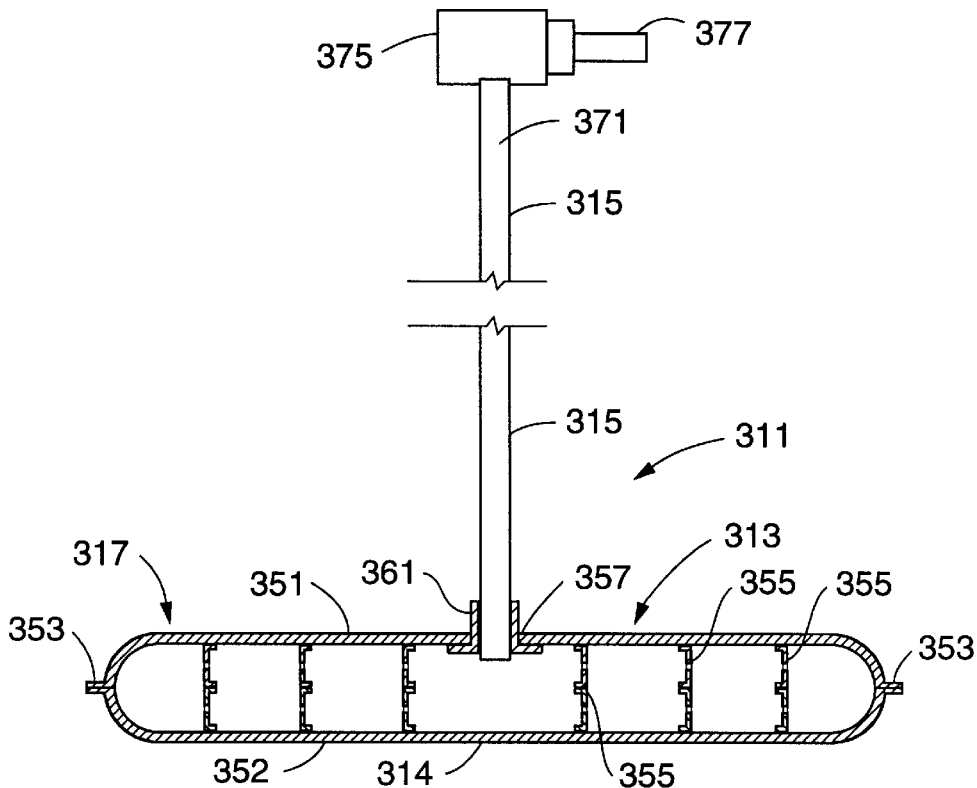
FIG. 11C is a cross-sectional view of the auxiliary retractor according to the invention in its inflated state.

The structure of the auxiliary retractor 311 is shown in the cross-sectional view shown in FIG. 11C. The auxiliary retractor includes the inflatable element 313, and the retraction tube 315. The inflatable element is similar to the body wall engaging element 13 shown in FIGS. 1A–1D, but has a reduced height. The inflatable element is made by welding the upper envelope half 351 to the lower envelope half 352 at their peripheries 353, in a manner similar to that described above. The upper and lower envelope halves are also interconnected by the baffles 355. The baffles control the shape of the inflatable element when the latter is inflated, and provide the inflatable element with that broad, flat, lower surface 314 that transfers the retraction force to the organ being retracted. The envelope halves and baffles are preferably made from the polyester/polyurethane composite film described above.

The retraction tube 315 is a single-wall tube, and is longer than the lifting tube 15 of the inflatable retraction apparatus 11 shown in FIGS. 1A–1D. The retraction tube is attached only to the upper envelope half 351 of the retracting element 313. Consequently, only the upper envelope half is formed with a retracting tube mounting hole 357. The retracting tube mounting 361 is inserted into the retracting tube mounting hole and is RF welded into place. The retracting tube 315 is then attached to the retracting tube mounting using a suitable adhesive.

Using a single-wall tube for the retraction tube 315 reduces the diameter of the auxiliary retractor in its packaged state compared with that of the inflating lifting apparatus 11 in the packaged state. This enables the packaged auxiliary retractor to fit through the bore 71 of the lifting tube 15 of the inflating lifting device. Not attaching the retracting tube 315 to the lower envelope half 352 provides a separation between the retracting surface 314 and the distal end of the retracting tube approximately equal to the height of the retracting element 313. This separation substantially reduces the possibility of the organs retracted by the auxiliary retractor coming into contact with any part of the auxiliary retractor other than the broad, relatively compliant, retracting surface 314.

The proximal end of the retracting tube 315 is fitted with the port 375, which carries the valve 377, which is preferably a pressure control valve, as described above. The port may include a flap-valve (not shown) on its rear face to allow an endoscope (not shown) to be inserted into the bore 371 of the retracting tube. The distal end of the endoscope enters the interior of the retracting element 313 to provide visualization through the relatively transparent material of the lower envelope half 352.

Alternatively, a non-pressurized endoscope access may be provided by using a small-diameter double-wall tube (not shown) as the retracting tube. Such a tube would have a inner bore with a closed distal end and an open proximal end. The diameter of the inner bore would be large enough to accommodate a small-diameter endoscope. The endoscope would provide viewing through the relatively transparent material of the lower envelope half 352. Inflation fluid would pass into the retracting element 313 through the lumen between the inner and outer walls of the retraction tube. With this alternative construction, no flap-valve is required on the port 375.

Figure 11D:
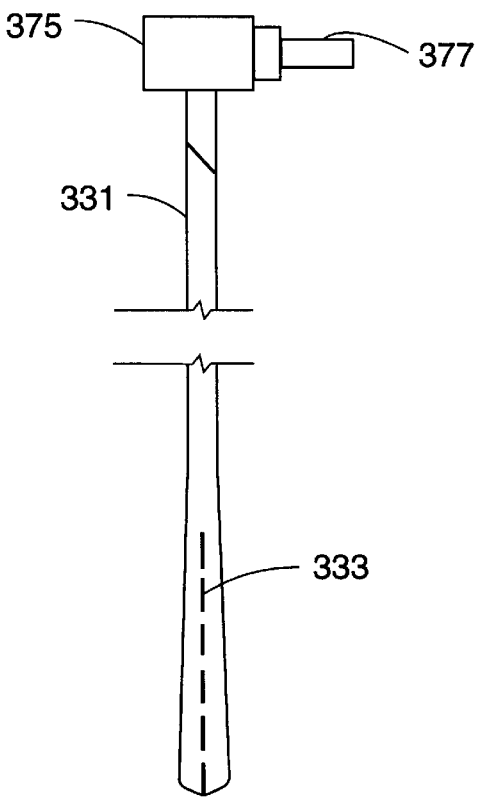
FIG. 11D is a side view of the auxiliary retractor according to the invention in its packaged state.

FIG. 11D shows the auxiliary retractor in its packaged state 301. The auxiliary retractor is packaged in a manner similar to that described above with reference to FIGS. 2A and 2B. The envelope 317 of the retraction element is retained in its packaged state by the sleeve 331. The longitudinal perforations 333 in the sleeve 331 are ruptured by partially inflating the retraction element to release the envelope 317 from its packaged state.

Figure 12A:
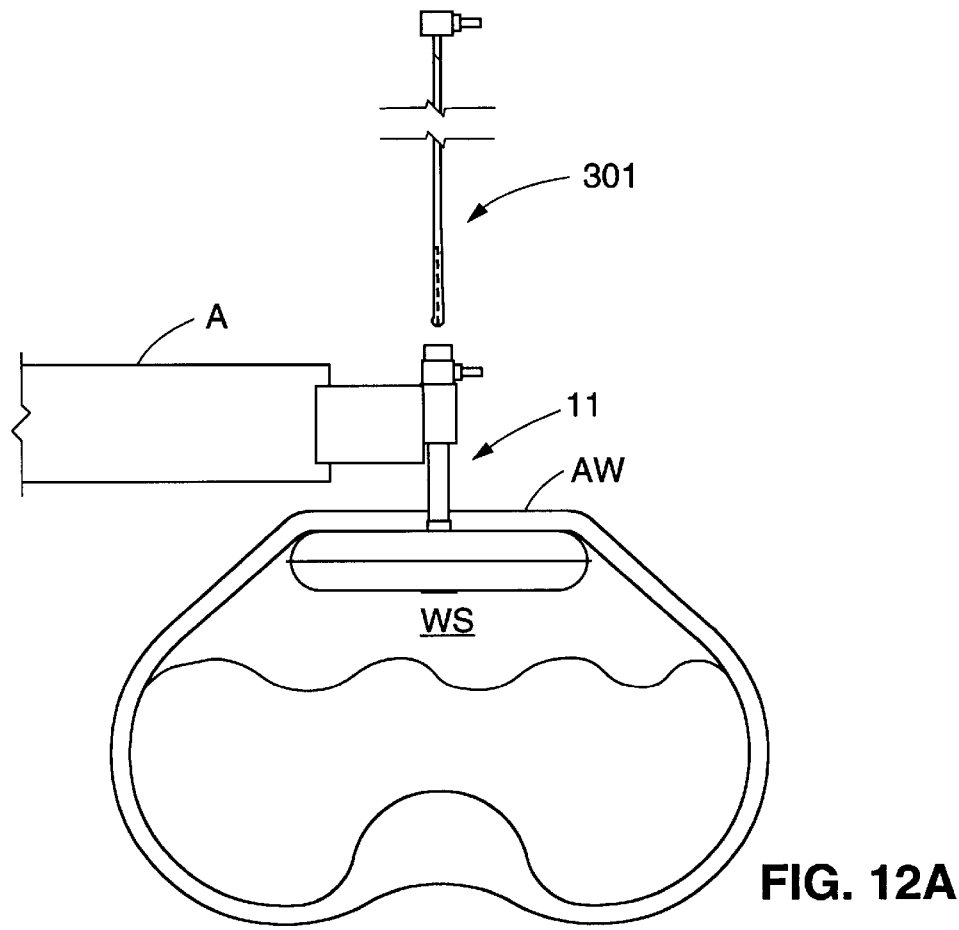
FIG. 12A–12D are transverse cross-sectional views of the human abdomen illustrating the method according to the invention of using the auxiliary retractor according to the invention to retract an organ underlying the abdominal wall after the inflating lifting device according to the invention has been used to lift the abdominal wall.
Figure 12B:
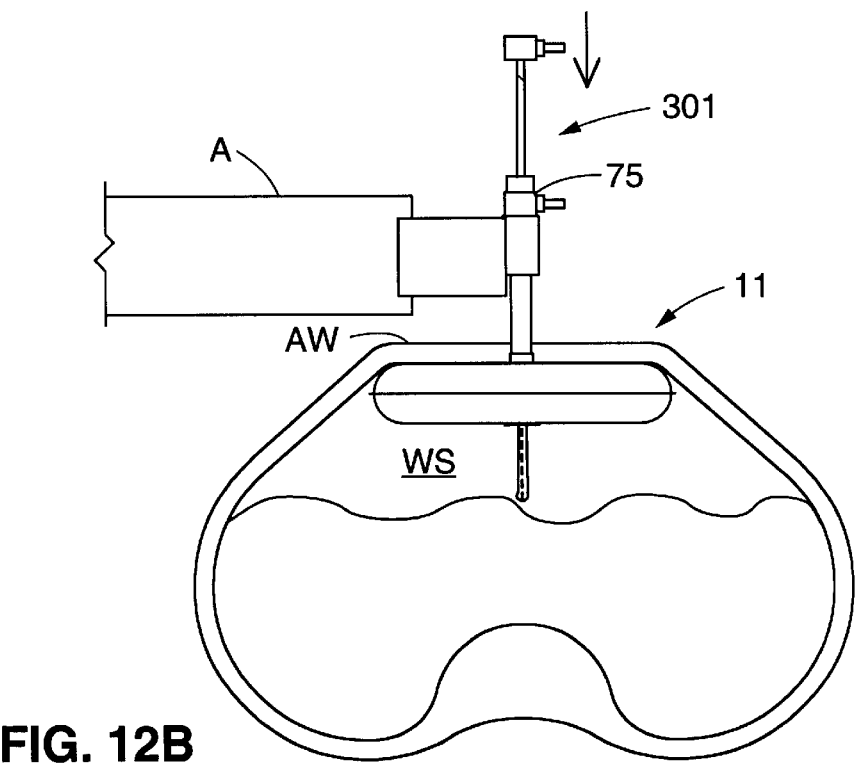

The auxiliary retractor 311 is used together with the inflating lifting apparatus 11 to provide auxiliary retraction using to the method illustrated in FIGS. 12A–12D. In FIG. 12A, the abdominal wall has been raised by the inflating lifting apparatus 11 using the procedure described above. The auxiliary retractor 301 in the packaged state shown in FIG. 11C is then inserted through the port 75 into the bore of the lifting tube 15. The auxiliary retractor is advanced through the inner bore of the lifting tube of the inflating lifting apparatus until the junction between the retraction tube 315 and the upper envelope half 351 emerges from the distal end of the inner bore of the lifting tube. This is shown in FIG. 12B.

Figure 12C:
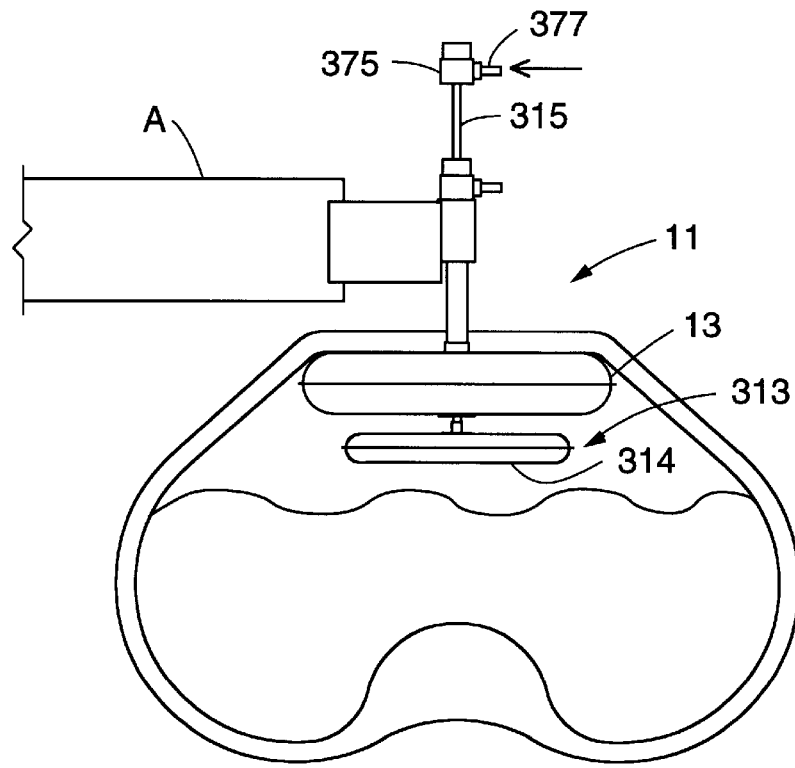

The inflating apparatus 121 (FIG. 9) is then connected to the valve 377, and the retracting element 313 is partially inflated to rupture the sleeve 331. After the sleeve 331 has ruptured, the retracting element is fully inflated, as shown in FIG. 12C.

Figure 12D:
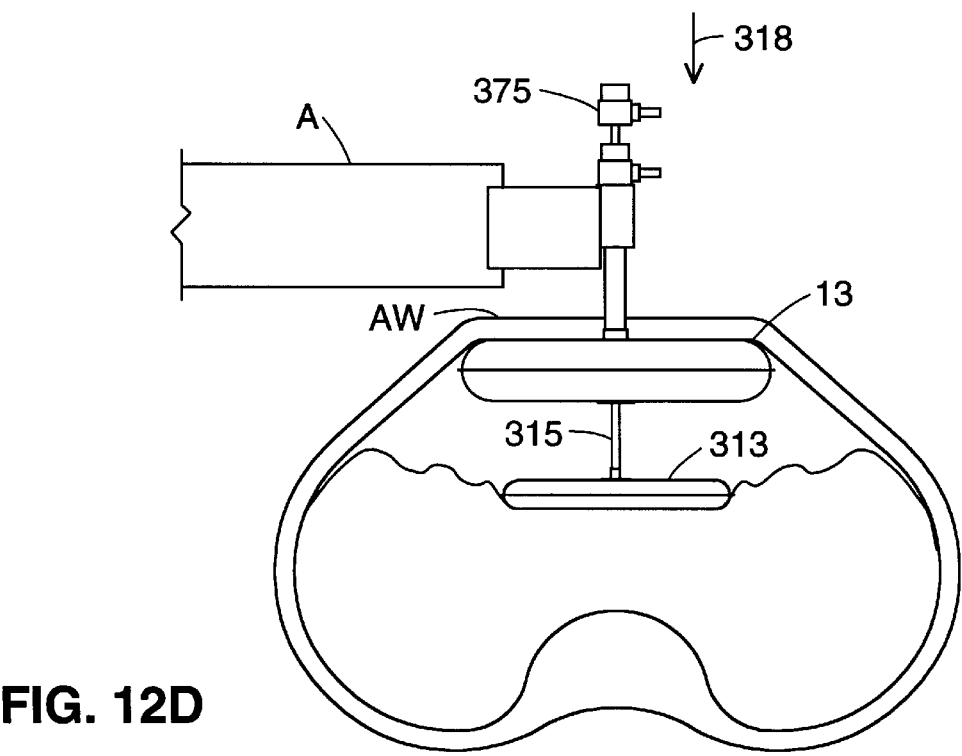

When the retraction element 313 is fully inflated, the retraction tube 315 is then slid distally (indicated by the arrow 318) relative to the lifting tube, as shown in FIG. 12D. This moves the retraction element distally to apply a retraction force to retract the organs O underlying the abdominal wall. The retraction force is distributed uniformly over the broad retraction face 314 of the auxiliary retractor, which minimizes the retraction pressure applied to the underlying organs, and minimizes the possibility of the retraction process causing trauma.

After the treatment procedure, the retraction element is deflated and evacuated in a manner similar to that described above with respect to the inflating lifting device 11. The auxiliary retractor is then withdrawn from the lifting tube 15 of the inflating lifting device, and the inflating lifting apparatus is withdrawn from the body cavity using the method described above.

The auxiliary retractor 311 may be used alone, without the inflating lifting device 11, to retract organs underlying the body wall. The auxiliary retractor is deployed under the body wall adjacent the organ to be retracted. A procedure similar to that illustrated in FIGS. 10A–10D is used. Then, when the retraction element 313 is fully inflated, the retraction tube 315 is manipulated to move the retraction tube distally to cause the retraction element to retract the organ. To improve the "feel" of the auxiliary retractor, a trocar tube or other suitable cannula (not shown) may be driven through the body wall prior to deploying the auxiliary retractor. The distal part of the auxiliary retractor would then be inserted into the body cavity through the trocar or cannula.

Although illustrative embodiments of the invention have been described herein in detail, it is to be understood that the invention is not limited to the precise embodiments described, and that various modifications may be practiced within the scope of the invention defined by the appended claims.

We claim:

1. A method for lifting a body wall by applying an external lifting force to a large area of the body wall through a laparoscopic incision, the method comprising the steps of:

providing a lifting device, the lifting device including a body wall engaging element having a bore and further including a packaged state in which the body wall engaging element forms a package capable of passing through the laparoscopic incision, and a lifting member, the lifting member including a distal portion whereto the body wall engaging element is connected, and a proximal portion and further providing an inflatable retractor;

with the body wall engaging element in the packaged state, advancing the body wall engaging element through the laparoscopic incision;

inflating the body wall engaging element to an inflated state to release the body wall engaging element from the packaged state and to provide a plane lifting surface;

with the body wall engaging element oriented such that the plane lifting surface extends laterally of the distal portion of the lifting member, applying the external lifting force to the proximal portion of the lifting member to move the lifting surface into contact with the body wall;

passing the inflatable retractor in a packaged state through the bore from outside the body wall, inflating the inflatable retractor to an inflated state, and applying an external retraction force to the inflatable retractor in a direction substantially opposite to the direction of the lifting force, to retract tissue underlying the body wall using the inflated inflatable retractor.

2. The method of claim 1, wherein the inflatable retractor is provided to include:

a retraction element capable of passing in a packaged state through the bore of the lifting member, and being inflatable to the inflated state, the retraction element in the inflated state including a plane retraction surface, and an elongate operating member including a distal portion connected to the retraction element and capable of passing through the bore of the lifting member, and a proximal portion.

* * * * *